United States Patent
Sato et al.

(10) Patent No.: US 8,164,334 B2
(45) Date of Patent: Apr. 24, 2012

(54) POSITION DETECTION SYSTEM

(75) Inventors: Ryoji Sato, Hino (JP); Akio Uchiyama, Yokohama (JP); Atsushi Kimura, Akiruno (JP)

(73) Assignee: Olympus Corporation (JP)

( * ) Notice: Subject to any disclaimer, the term of this patent is extended or adjusted under 35 U.S.C. 154(b) by 611 days.

(21) Appl. No.: 12/088,985

(22) PCT Filed: Oct. 6, 2006

(86) PCT No.: PCT/JP2006/320062
§ 371 (c)(1),
(2), (4) Date: Jun. 22, 2009

(87) PCT Pub. No.: WO2007/043458
PCT Pub. Date: Apr. 19, 2007

(65) Prior Publication Data
US 2009/0295386 A1    Dec. 3, 2009

(30) Foreign Application Priority Data
Oct. 6, 2005 (JP) .................. 2005-294056

(51) Int. Cl.
*G01V 3/00* (2006.01)
(52) U.S. Cl. ...................... 324/309
(58) Field of Classification Search .......... None
See application file for complete search history.

(56) References Cited

U.S. PATENT DOCUMENTS

| 6,538,617 B2 * | 3/2003 | Rochelle | 343/788 |
| 7,026,927 B2 | 4/2006 | Wright et al. | 340/539.12 |
| 2005/0216231 A1 | 9/2005 | Aoki et al. | 702/183 |
| 2008/0275334 A1 * | 11/2008 | Berting | 600/424 |

FOREIGN PATENT DOCUMENTS

| JP | 2006-26391 | 2/2006 |
| JP | 2006-192252 | 7/2006 |
| WO | WO 2004/014225 | 2/2004 |

OTHER PUBLICATIONS

International Search Report mailed Dec. 26, 2006 in corresponding PCT International Application No. PCT/JP2006/320062.

* cited by examiner

*Primary Examiner* — Paresh Patel
(74) *Attorney, Agent, or Firm* — Ostrolenk Faber LLP

(57) ABSTRACT

A position detection system that does not require calibration measurement to be performed in advance and reduces the work required for detecting a position and so on is provided. The provided position detection system includes a device having a magnetic inductance coil; a drive coil that has a position-calculating frequency near a resonant frequency of the magnetic inductance coil and generates an alternating magnetic field which acts on the magnetic inductance coil; a plurality of magnetic-field sensors that is disposed outside the operating range of the device and detects an induced magnetic field generated by the magnetic inductance coil; amplitude-component detection section for detecting amplitude components whose phase is substantially orthogonal to the alternating magnetic field from the outputs of the magnetic sensors acquired by the plurality of magnetic sensors; and position analyzing section for calculating at least one of a position and an orientation of the device on the basis of the amplitude components.

21 Claims, 27 Drawing Sheets

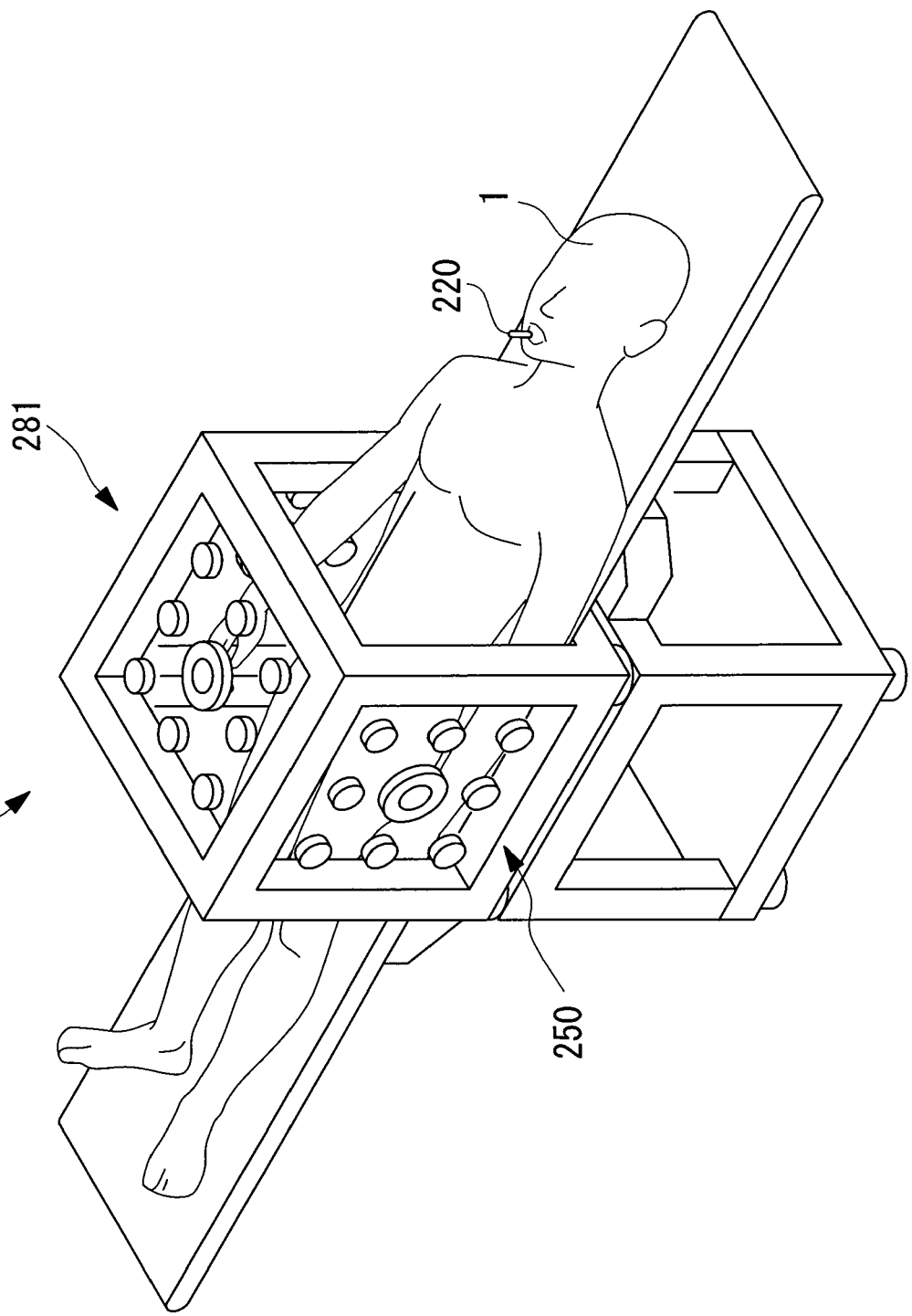

POSITION DETECTION SYSTEM

CROSS-REFERENCE TO RELATED APPLICATIONS

The present application is a 35 U.S.C. §§371 national phase conversion of PCT/JP2006/320062, filed Oct. 6, 2006, which claims priority of Japanese Patent Application No. 2005-294056, filed Oct. 6, 2005, the disclosure of which has been incorporated herein by reference. The PCT International Application was published in the Japanese language.

TECHNICAL FIELD

The present invention relates to a position detection system.

BACKGROUND ART

Medical devices such as capsule medical devices are swallowable medical devices that are swallowed by a subject to enter the subject's body, where they traverse a passage in the body cavity to capture images of a target site inside the passage in the body cavity. The capsule medical devices described above have a configuration in which an image-acquisition device that can perform the above-described medical procedure, for example, a CCD (Charge Coupled Device) that can acquire images or the like, is provided for performing image acquisition at the target site inside the passage in the body cavity.

However, the above-described capsule medical device has to be guided through the body cavity in order to reach a target site. To guide the capsule medical device, it is necessary to detect its position in the body cavity.

Therefore, techniques for detecting the position of capsule medical devices guided to sites whose positions cannot be visibly confirmed (body cavities or the like) (for example, refer to Patent Document 1) are proposed.

Patent Document 1:
PCT International Publication No. WO 2004/014225 Pamphlet
Patent Document 2:
U.S. Pat. No. 7,026,927

DISCLOSURE OF INVENTION

The above-mentioned Patent Document 1 discloses a position detection technique for a capsule medical device using a capsule medical device provided with a magnetic-field generating circuit including an LC resonant circuit connected to an AC power source and a detection device that is disposed outside the capsule medical device and that detects the magnetic field generated by the magnetic-field generating circuit. According to this technique, the magnetic-field generating circuit generates an externally directed magnetic field on the basis of the AC electric power supplied from the AC power source. In this way, the detection device can detect the position of the capsule medical device by detecting the magnetic field.

However, according to the above-described technique for position detection, a magnetic-field generating circuit including an LC resonant circuit connected to an AC power source is disposed inside the capsule medical device. Therefore, it is difficult to reduce the size of the capsule medical device, and thus, there is a problem in that it is difficult to produce a capsule medical device having a size that is easily swallowed by the subject. In contrast, if the size of the capsule medical device is reduced, the size of the AC power source is also reduced, thus limiting the electric power supplied to the magnetic-field generating circuit. Consequently, the intensity of the magnetic field generated by the magnetic-field generating circuit is reduced, and thus there is a problem in that position detection of the capsule medical device becomes more difficult. There is also a problem in that, since the life of the AC power source is shortened, the life of the capsule medical device is also shorted.

Furthermore, there is a known position detection technique for a capsule medical device using a capsule medical device including an LC resonant circuit formed of only a magnetic inductance coil and a capacitor, a drive coil that is disposed outside the subject's body for generating an induced electromotive force, and a plurality of magnetic-field sensors that is disposed outside and detects an induced magnetic field.

According to this technique, first the magnetic inductance coil in the LC resonant circuit generates an induced magnetic field by an induced electromotive force induced by the drive coil. Then, the position of the capsule medical device can be detected by detecting the induced magnetic field generated by the magnetic-field sensors. In other words, according to this technique, since the position of the capsule medical device can be detected without installing an AC power source inside the capsule medical device, the size of the capsule medical device can be easily reduced, position detection becomes easy, and the life of the device can be increased.

During this operation, the drive coil causes an alternating magnetic field having two different frequencies close to the resonant frequency of the LC resonant circuit to act upon the LC resonant circuit.

However, according to the above-described position detection technique, since the magnetic-field sensors simultaneously detect the driving magnetic field generated by the drive coil and the induced magnetic field generated by the magnetic inductance coil, it is difficult to detect the position of the capsule medical device because the induced magnetic field is lost in the driving magnetic field.

It is known that the induced magnetic field can be calculated by measuring only the driving magnetic field of the drive coils (calibration measurement) in advance, with the magnetic inductance coil being disposed outside the detection range, in order to remove only the driving magnetic field from the simultaneously detected driving magnetic field and induced magnetic field and by subtracting the measured driving magnetic field from the simultaneously detected driving magnetic field and the induced magnetic field.

The frequency of the driving magnetic field to be measured by calibration must be the same as the frequency of the driving magnetic field used during detection of the position of the capsule medical device.

However, the problem with the above-described method is that it is necessary to always carry out, in advance, calibration measurement of the driving magnetic field to be used, thus making the position detection complicated.

The frequency of the driving magnetic field is set based on the resonant frequency of the LC resonant circuit. The resonant frequency is affected by the difference in the characteristics of the magnetic inductance coil and the capacitor included in the LC resonant circuit. In other words, each individual capsule medical device has an LC resonant circuit with a different resonant frequency. Therefore, calibration measurement of the driving magnetic field must be carried out for each individual capsule medical device.

Therefore, there is a problem in that calibration measurement cannot be carried out until it is determined which capsule medical device is to be used. Otherwise there is a problem in that calibration measurement must be carried out for all frequencies of the driving magnetic field that might be used for position detection of the capsule medical device, thus making the position detection of the capsule medical device complicated.

The positional relationship between the drive coils and the magnetic-field sensors must be fixed after carrying out calibration measurement; if the positional relationship between the drive coils and the magnetic-field sensors changes, there is a problem in that position detection of the capsule medical device or the like cannot be carried out.

To solve such problems, there is a proposed technique in which two different periods, i.e., a period of activating the drive coil and a period of deactivating the drive coil, are set (for example, refer to Patent Document 2). Patent Document 2 discloses a technique for position detection without calibration measurement by generating an induced magnetic field at the magnetic inductance coil during the period of activating the drive coil, and then by detecting only the induced magnetic field generated at the magnetic inductance coil by stopping the driving of the drive coil. According to this technique, the magnetic field generated by the drive coil disappears when the drive coil is deactivated. However, even when the drive coil is deactivated, the induced magnetic field generated by the magnetic inductance coil is maintained for a while. By detecting this magnetic field with the magnetic-field sensors, the position of the magnetic inductance coil can be detected.

However, with this technique of detecting a position by deactivating the drive coil, the position can only be detected while the drive coil is deactivated. Therefore, there is a problem in that the number of possible position detections during a predetermined amount of time decreases.

The present invention has been conceived in light of the problems described above. Accordingly, it is an object of the present invention to provide a position detection system that does not require calibration measurement to be carried out in advance, enables a less complicated process of position detection, and prevents a reduction in the number of necessary position detection operations. It is another object to provide a position detection system that is capable of detecting the position of a capsule medical device and the like even when the positional relationship between the drive coil and the magnetic-field sensors changes.

To achieve the above-described objects, the present invention provides the following solutions.

In one aspect of the present invention provides a position detection system including a device having a magnetic inductance coil; a drive coil configured to generate an alternating magnetic field; a plurality of magnetic-field sensors disposed outside an operating range of the device and configured to detect an induced magnetic field generated by the magnetic inductance coil, which receives the alternating magnetic field; a frequency determining section configured to determine a position-calculating frequency on the basis of a resonant frequency of the magnetic inductance coil; amplitude-component detection section for detecting at least one of amplitude components substantially orthogonal to the alternating magnetic field and amplitude components having substantially the same phase as the alternating magnetic field from outputs of the plurality of magnetic-field sensors at the position-calculating frequency; and position analyzing section for calculating at least one of a position and an orientation of the device on the basis of the amplitude components.

According to this aspect of the present invention, the amplitude-component detection section detects amplitude components that have a phase orthogonal to or the same as the alternating magnetic field from the outputs of the magnetic-field sensors, and the position analyzing section can calculate at least one of the position and the orientation of the device on the basis of the amplitude components. In other words, without stopping the drive coil, the amplitude-component detection section can separate amplitude components that include only information associated with the position and orientation of the device and that do not include information associated with the position and orientation of the drive coil from the outputs of the magnetic-field sensors that have received the magnetic fields from the drive coil and the magnetic inductance coil. Therefore, at least one of the position and orientation of the device can be calculated without measuring the outputs of the plurality of magnetic-field sensors when only the alternating magnetic field acts on the plurality of magnetic-field sensors (calibration measurement) and without reducing the number of detection operations performed during a predetermined amount of time.

Since the magnetic inductance coil generates an induced magnetic field from the alternating magnetic field, a power source does not have to be added to the magnetic inductance coil. Therefore, the number of components installed in the device can be reduced. Furthermore, since a power source installed in the device is not used to generate a magnetic field used for position detection of the device, the life of the device is not affected by the life of such a power source.

The amplitude-component detection section can detect amplitude components that have the same phase as the alternating magnetic field in the output from the magnetic-field sensors, and the position analyzing section can calculate the position and so on of the device on the basis of the amplitude components.

In this aspect of the present invention, it is preferable that the frequency determining section determine the position-calculating frequency by acquiring information about the resonant frequency in advance.

According to this aspect of the present invention, since the position-calculating frequency obtains a resonant frequency in advance, the frequency of the alternating magnetic field does not have to be swept in a frequency band including the position-calculating-frequency. Therefore, the amount of time required for calculating at least one of the position and the orientation of the device can be reduced.

In this aspect of the present invention, it is preferable that the frequency determining section detect a change in the resonant frequency and determine the position-calculating frequency on the basis of the change.

According to this aspect of the present invention, since the frequency determining section can detect a change in the resonant frequency of the magnetic inductance coil, the relationship between the resonant frequency and the position calculating frequency can be maintained constant. Since the position-calculating-frequency determining section can detect a change in the resonant frequency, for example, when the resonant frequency changes due to a change in the temperature of the magnetic inductance coil, at least one of the position and the orientation of the device can be calculated.

In this aspect of the present invention, it is preferable that, when the amplitude-component detection section uses Fourier transformation to repeatedly calculate at least one of the position and the orientation of the device on the basis of the detected amplitude components, the amplitude-component detection section perform Fourier transformation while assuming that the difference between the timing of starting Fourier transformation and the phase of the alternating magnetic field generated by the drive coil is constant.

According to this aspect of the present invention, amplitude components can be quickly and accurately detected by using Fourier transformation for detecting the amplitude components with the amplitude-component detection section.

By maintaining a constant relative relationship between the timing of starting Fourier transformation and the phase of the alternating magnetic field, variations in the calculation of at least the position and the orientation can be suppressed.

With this aspect of the present invention, it is preferable that the drive coil and the magnetic-field sensors be provided as separate bodies.

According to this aspect of the present invention, since the drive coil and the magnetic-field sensors are provided as separate bodies, the drive coil and the magnetic-field sensors can be moved independently.

In this aspect of the present invention, it is preferable that the plurality of magnetic-field sensors be provided as a single body.

According to this aspect of the present invention, since the plurality of magnetic-field sensors is provided as a single body, the relative positional relationship of the magnetic-field sensors is fixed.

This aspect of the present invention preferably includes a drive-coil driver configured to change at least one of the direction and the intensity of the alternating magnetic field generated at the drive coil in accordance with the relative position of the drive coil and the magnetic inductance coil.

According to this aspect of the present invention, since the drive coil driver changes at least one of the direction and the intensity of the alternating magnetic field generated at the drive coil in accordance with the relative position of the drive coil and the magnetic inductance coil, an induced magnetic field can be reliably generated at the magnetic inductance coil.

In other words, the relative relationship between the direction of the alternating magnetic field generated by the drive coil and the direction of the magnetic inductance coil can be prevented from being set in a relative relationship that makes it difficult to generate an induced magnetic field at the magnetic inductance coil.

With this aspect of the present invention, it is preferable that the drive coil and the magnetic-field sensors be attached to a subject disposed in the operating range.

According to this aspect of the present invention, at least one of the position and the orientation of the device can continuously be detected even when for example, the subject moves by attaching the drive coil and the magnetic-field sensors to the subject.

With this aspect of the present invention, it is preferable that, when a plurality of the devices is used simultaneously, the magnetic inductance coils installed in the devices be set to different resonant frequencies.

According to this aspect of the present invention, since a plurality of devices is provided and the resonant frequencies of the magnetic inductance coils installed in the devices differ, the positions and orientations of the plurality of devices can be detected simultaneously.

In another aspect, the present invention provides a guidance system including a position detection system according to the above-described aspect of the present invention; a guidance magnet installed in the device; guidance-magnetic-field generating section for generating a guidance magnetic field that acts on the guidance magnet; and guidance-magnetic-field-direction control section for controlling the direction of the guidance magnetic field.

According to this aspect of the present invention, the position and so on of the device can be determined by the position detection system of the present invention, and the device can be guided to a predetermined position by the guidance-magnetic-field generating section and the guidance-magnetic-field-direction control section.

In this aspect of the present invention, it is preferable that the guidance-magnetic-field generating section include three pairs of electromagnets that are disposed facing each other in an orthogonally intersecting manner; a space where the subject lies be provided on the inner side of the electromagnets; and the drive coil and the magnetic-field sensors be disposed around the space where the subject lies.

According to this aspect of the present invention, the position of the device introduced into the subject is detected, and the device is guided to a predetermined position.

In this aspect of the present invention, it is preferable that a helical part configured to convert a rotational force around the longitudinal axis of the device to a propulsive force along the longitudinal axis be provided on an outer surface of the device.

According to this aspect of the present invention, the device rotates around the longitudinal axis and moves along the longitudinal axis by the action of the helical part.

In this aspect of the present invention, it is preferable that the device comprise a capsule medical device.

According to this aspect of the present invention, since the device is a capsule medical device, the device can be introduced into the body of the subject and can perform medical treatment inside the body.

In another aspect, the present invention provides a position detection system including a device having a magnetic inductance coil; a drive coil configured to generate an alternating magnetic field; a plurality of magnetic-field sensors and configured to detect an induced magnetic field generated by the magnetic inductance coil, which receives the alternating magnetic field; a frequency determining section configured to determine a position-calculating frequency on the basis of a resonant frequency of the magnetic inductance coil; measurement-reference-value calculating section for determining a measurement reference value at the position-calculating frequency on the basis of outputs from the magnetic-field sensors output when the alternating magnetic field and the induced magnetic field are applied at a second frequency away from the position-calculating frequency; and position analyzing section for calculating at least one of a position and an orientation of the device on the basis of a difference between the outputs from the magnetic-field sensors output when the alternating magnetic field and the induced magnetic field are applied at the position-calculating frequency and the measurement reference value.

According to this aspect of the present invention, the measurement-reference-value calculating section determines a measurement reference value at the position-calculating frequency on the basis of output values from the magnetic-field sensors output at the position-calculating frequency and the second frequency, and the position analyzing section calculates at least one of a position and an orientation of the device on the basis of a difference between the output values from the magnetic-field sensors output when the alternating magnetic field and the induced magnetic field act on the magnetic-field sensors and the measurement reference value. In other words, by determining a measurement reference value at the position-calculating frequency, output values associated with the induced magnetic field can be extracted from the output values of the magnetic-field sensors when the alternating magnetic field and the induced magnetic field act on the magnetic-field sensors, and at least one of the position and the orientation of the device can be calculated.

Therefore, at least one of the position and orientation of the device can be calculated and position detection of the device can be performed without measuring the outputs of the plurality of magnetic-field sensors when only the alternating magnetic field acts on the plurality of magnetic-field sensors (calibration measurement).

Since the magnetic inductance coil generates an induced magnetic field from the alternating magnetic field, a power source does not have to be added to the magnetic inductance coil. Therefore, the number of components installed in the device can be reduced. Furthermore, since the power source installed in the device is not used to generated a magnetic field used for position detection of the device, the life of the device is not affected by the life of the power source.

In this aspect of the present invention, it is preferable that the position-calculating frequency be two different frequencies.

According to this aspect of the present invention, since the position-calculating frequency is two different frequencies, by using the output values of the magnetic-field sensors including the amplitude components at these two position-calculating frequencies, the error of the measured values can be cancelled out, compared with when output values at one frequency is used, and thus, the accuracy of the calculated position and so on of the device can be improved.

In this aspect of the present invention, it is preferable that the frequency determining section determine the position-calculating frequency by acquiring information about the resonant frequency of the magnetic inductance coil in advance.

According to this aspect of the present invention, since the frequency determining section acquires information about the resonant frequency of the magnetic inductance coil, it is easy to determine the position-calculating frequency in advance.

In this aspect of the present invention, it is preferable that the position-calculating-frequency determining section detect a change in the resonant frequency and determine the position-calculating frequency on the basis of the change.

According to this aspect of the present invention, since the position-calculating-frequency determining section detects a change in the resonant frequency of the magnetic inductance coil, a constant relationship between the resonant frequency of the magnetic inductance coil and the position-calculating frequency can be maintained.

In this aspect of the present invention, it is preferable that the drive coil and the magnetic-field sensors be provided as separate bodies.

According to this aspect of the present invention, since the drive coil and the magnetic-field sensors are provided as separate bodies, the drive coil and the magnetic-field sensors can be moved independently.

In this aspect of the present invention, it is preferable that the plurality of magnetic-field sensors be provided as a single body.

According to this aspect of the present invention, since the plurality of magnetic-field sensors is provided as a single body, the relative positional relationship of the magnetic-field sensors is fixed.

In this aspect of the present invention, it is preferable that, when a plurality of the devices is used simultaneously, the magnetic inductance coils installed in the devices be set to different resonant frequencies.

According to this aspect of the present invention, since a plurality of devices is provided and the resonant frequencies of the magnetic inductance coils installed in the devices differ, the positions and orientations of the plurality of devices can be detected simultaneously.

In this aspect of the present invention, it is preferable that the device comprise a capsule medical device.

According to this aspect of the present invention, since the device is a capsule medical device, the device can be introduced into the body of the subject and can perform medical treatment inside the body.

With a first position detection system according to the present invention, the amplitude-component detection section can detect amplitude components, and the position analyzing section can calculate at least one of the position and orientation of the device. Therefore, there is an advantage in that at least one of the position and orientation of the device can be calculated without measuring the outputs of the plurality of magnetic-field sensors when only the alternating magnetic field acts on the plurality of magnetic-field sensors (calibration measurement), and the amount of work required for detecting the position and so on can be reduced.

With a second position detection system according to the present invention, the measurement-reference-value calculating section can determine a measurement reference value at a position-calculating frequency, and the position analyzing section can calculate at least one of a position and an orientation of the device on the basis of a difference between the output values from the magnetic-field sensors output when the alternating magnetic field and the induced magnetic field act on the magnetic-field sensors and the measurement reference value. Therefore, there is an advantage in that at least one of the position and orientation of the device can be calculated without measuring the outputs of the plurality of magnetic-field sensors when only the alternating magnetic field acts on the plurality of magnetic-field sensors (calibration measurement), and the amount of work required for detecting the position and so on can be reduced.

BRIEF DESCRIPTION OF DRAWINGS

FIG. 18A is a schematic view illustrating the structure of the position detection system shown in FIG. 15.

EXPLANATION OF REFERENCE SIGNS 10, 110, 210, 310, 410, and 510: position detection system
20: capsule endoscope (device, capsule medical device)
50: position detection device (amplitude-component detection section, position analyzing section)
50A: amplitude-component detection section (amplitude-component detection section)
50B: position-calculating-frequency determining section (position-calculating-frequency determining section)
50C: position analyzing section (position analyzing section)
51: drive coils (drive coils)
52: sense coils (magnetic field sensors)
150 and 250: position detection device (amplitude-component detection section, position-calculating-frequency determining, position analyzing section, drive-coil driver)
450 and 550: position detection device (position-calculating-frequency determining section, reference-value-calculating-frequency determining section, measurement-reference-value calculating section, position analyzing means)
451: position-calculating-frequency determining section
452: reference-value-calculating-frequency determining section (reference-value-calculating-frequency determining section)
453: measurement-reference-value calculating section (measurement-reference-value calculating section)
454: position analyzing section (position analyzing section)
250: position detection device (guidance-magnetic-field-direction control section)
701, 702, 703, 704, and 705: electromagnet (guidance-magnetic-field generating section)
$f_H$ and $f_L$: position calculating frequency
$f_1$: reference-value calculating frequency (second frequency)

BEST MODE FOR CARRYING OUT THE INVENTION

First Embodiment

A position detection system according to a first embodiment of the present invention will be described below with reference to FIGS. 1 to 10.

Figure 1:
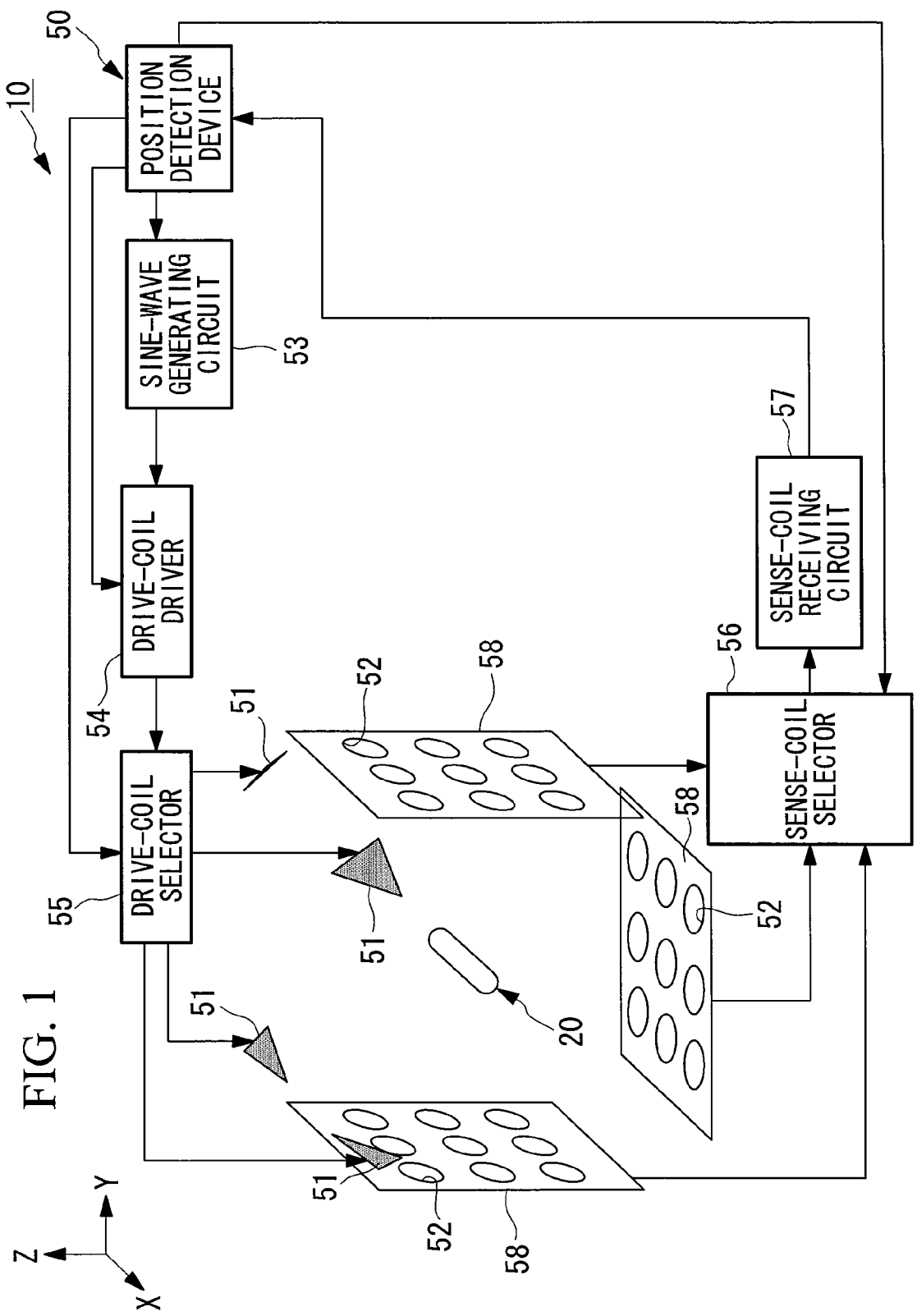
FIG. 1 is a schematic view illustrating the overall structure of a position detection system according to a first embodiment of the present invention.
Figure 2:
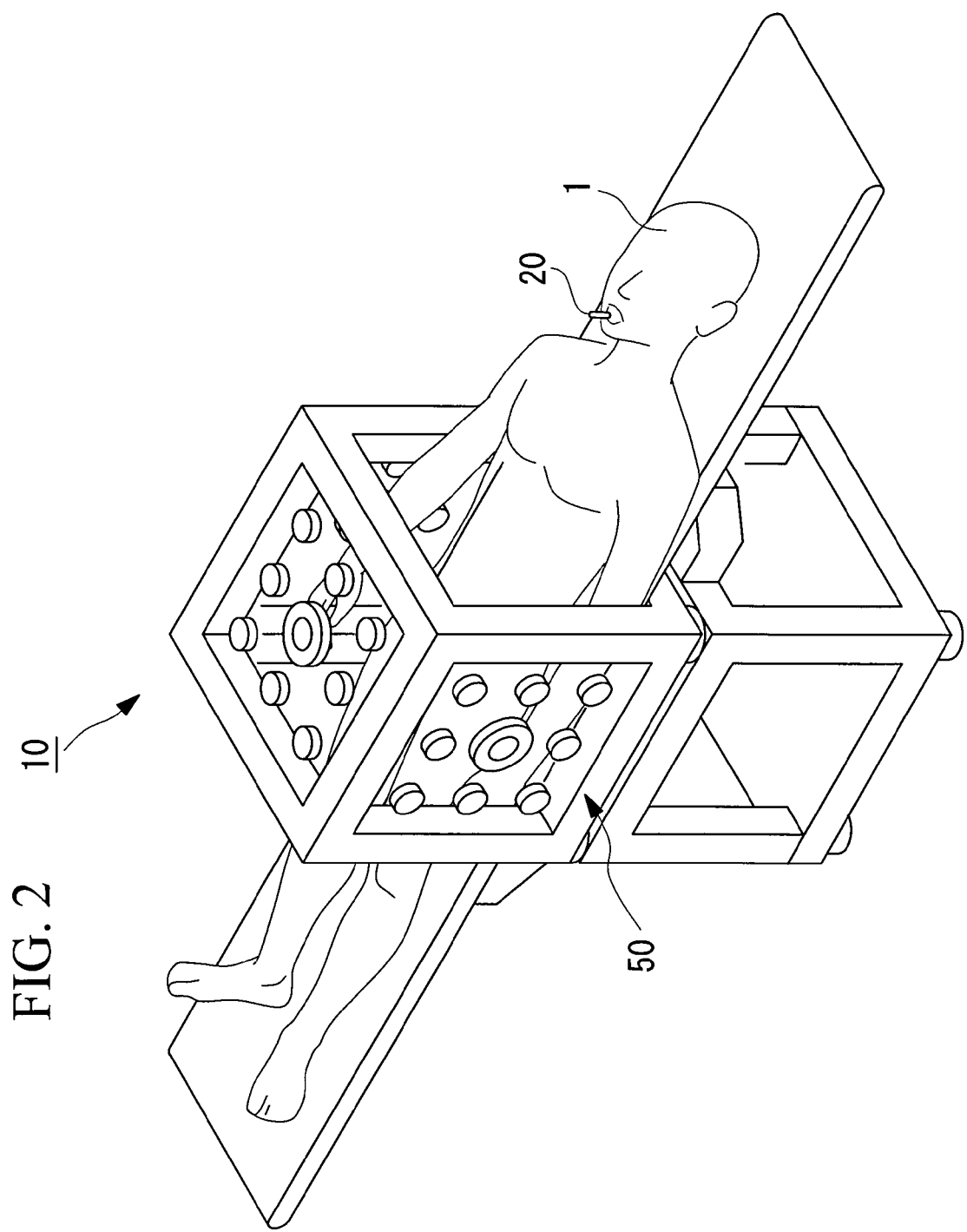
FIG. 2 is a perspective view illustrating the exterior of the position detection system shown in FIG. 1.

FIG. 1 is a schematic view illustrating the overall structure of a position detection system according to this embodiment. FIG. 2 is a perspective view illustrating the exterior of the position detection system shown in FIG. 1.

As shown in FIGS. 1 and 2, a position detection system 10 is mainly formed of a capsule endoscope (device, capsule medical device) 20, which is a capsule medical device introduced into a body cavity of a subject 1, per oral or per anus, to optically image an internal surface of a passage in the body cavity and wirelessly transmit an image signal, and a position detection device (amplitude-component detection means, position analyzing section) 50 that detects the position of the capsule endoscope 20. The capsule medical device is not limited to the above-described capsule endoscope; instead, it may be a capsule medical device that administers a drug at a predetermined site in the body cavity or obtains a sample, such as body fluid, or biological information.

As shown in FIG. 1, the position detection device 50 is electrically connected to drive coils (drive coils) 51 that generate an induced magnetic field at magnetic induction coils, described below, in the capsule endoscope 20 and sense coils (magnetic-field sensors) 52 that detect the induced magnetic field generated at the magnetic induction coils. The position detection device 50 calculates the position of the capsule endoscope 20 on the basis of the induced magnetic field detected by the sense coils 52 and controls the alternating magnetic field formed by the drive coils 51.

The position detection device 50 is provided with an amplitude-component detection section (amplitude-component detection section) 50A that detects an amplitude component by separating at least one of an imaginary part of an AC voltage, which is an amplitude component that is substantially orthogonal to an AC voltage output from a sense coil 52 (output of a magnetic-field sensor), and a real part of an AC voltage, which is an amplitude component having substantially the same phase; a position-calculating-frequency determining section (position-calculating-frequency determining section) 50B that determines the position-calculating frequency of the capsule endoscope 20; and a position analyzing section (position analyzing section) 50C that calculates at least one of the position and the orientation of the capsule endoscope 20 on the basis of the amplitude component.

Between the position detection device 50 and the drive coils 51 there are provided a sine-wave generating circuit 53 that generates an AC current based on the output from the position detection device 50; a drive-coil driver 54 that amplifies the AC current input from the sine-wave generating circuit 53 based on the output from the position detection device 50; and a drive-coil selector 55 that supplies the AC current to a drive coil 51 selected on the basis of the output from the position detection device 50.

Between the sense coils 52 and the position detection device 50 there are provided a sense-coil selector 56 and a sense-coil receiving circuit 57. The sense-coil selector 56 selects an AC current containing position information about the capsule endoscope 20 output from a specific sense coil 52 of the plurality of sense coils 52 on the basis of the output from the position detection device 50. The sense-coil receiving circuit 57 extracts an amplitude value of an AC voltage from the AC current that has passed through the sense-coil selector 56 and outputs the amplitude value to the position detection device 50.

Figure 3:
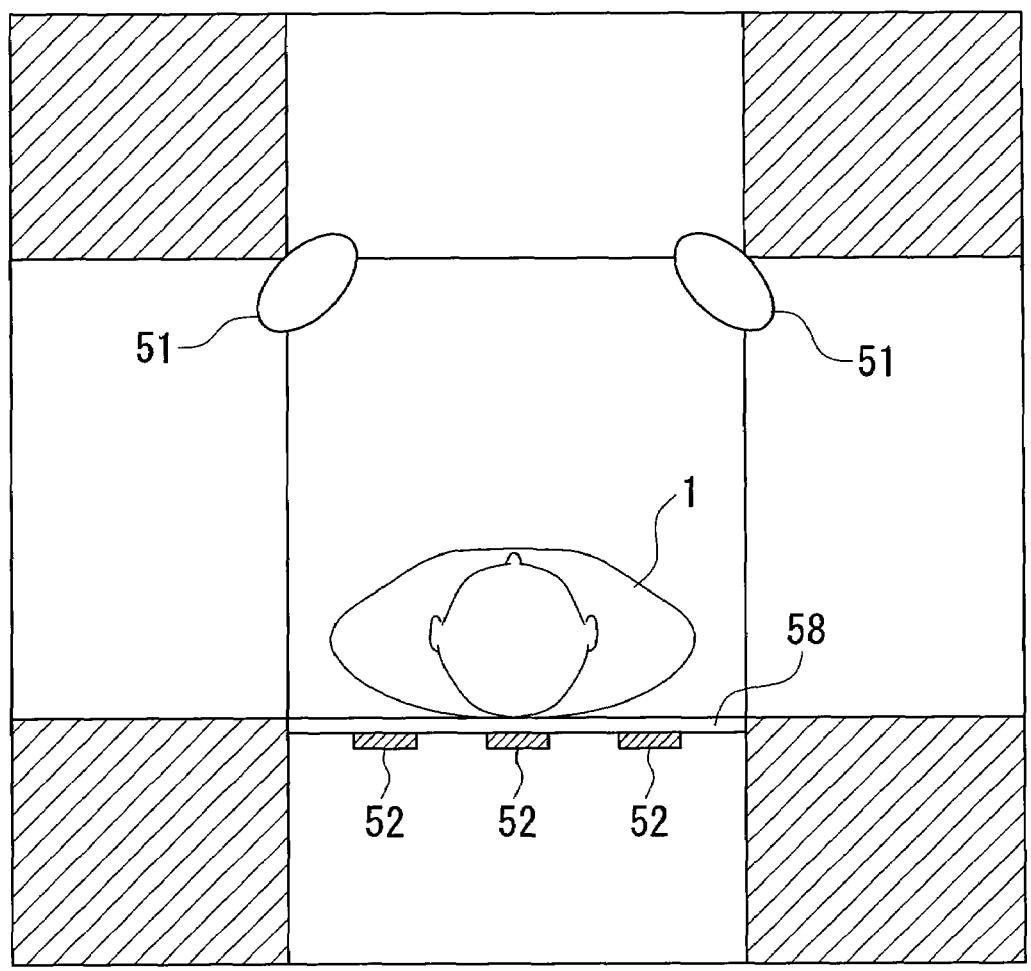
FIG. 3 is a schematic view illustrating a cross-section of a capsule endoscope system shown in FIG. 1.

FIG. 3 is a schematic view illustrating a cross-section of a capsule endoscope system shown in FIG. 1.

Here, as shown in FIGS. 1 and 3, the drive coils 51 are positioned at an angle at the four upper (in the positive direction of the Z-axis) corners of the substantially rectangular operating space where the subject 1 lies. The drive coils 51 form substantially triangular coils. By disposing the drive coils 51 at the top in this way, it is possible to prevent interference between the drive coils 51 and the subject 1.

The drive coils 51 may be substantially triangular coils, as mentioned above, or it is possible to use coils of various shapes, such as circular coils, etc.

The sense coils 52 are formed as air-core coils and are supported by three planar coil-supporting parts 58 that are disposed at positions facing the drive coils 51 and at positions mutually opposing each other in the Y-axis direction, with the operating space of the capsule endoscope 20 being disposed therebetween. Nine of the sense coils 52 are arranged in the form of a matrix in each coil-supporting part 58, and thus a total of 27 sense coils 52 are provided in the position detection device 50.

Figure 4:
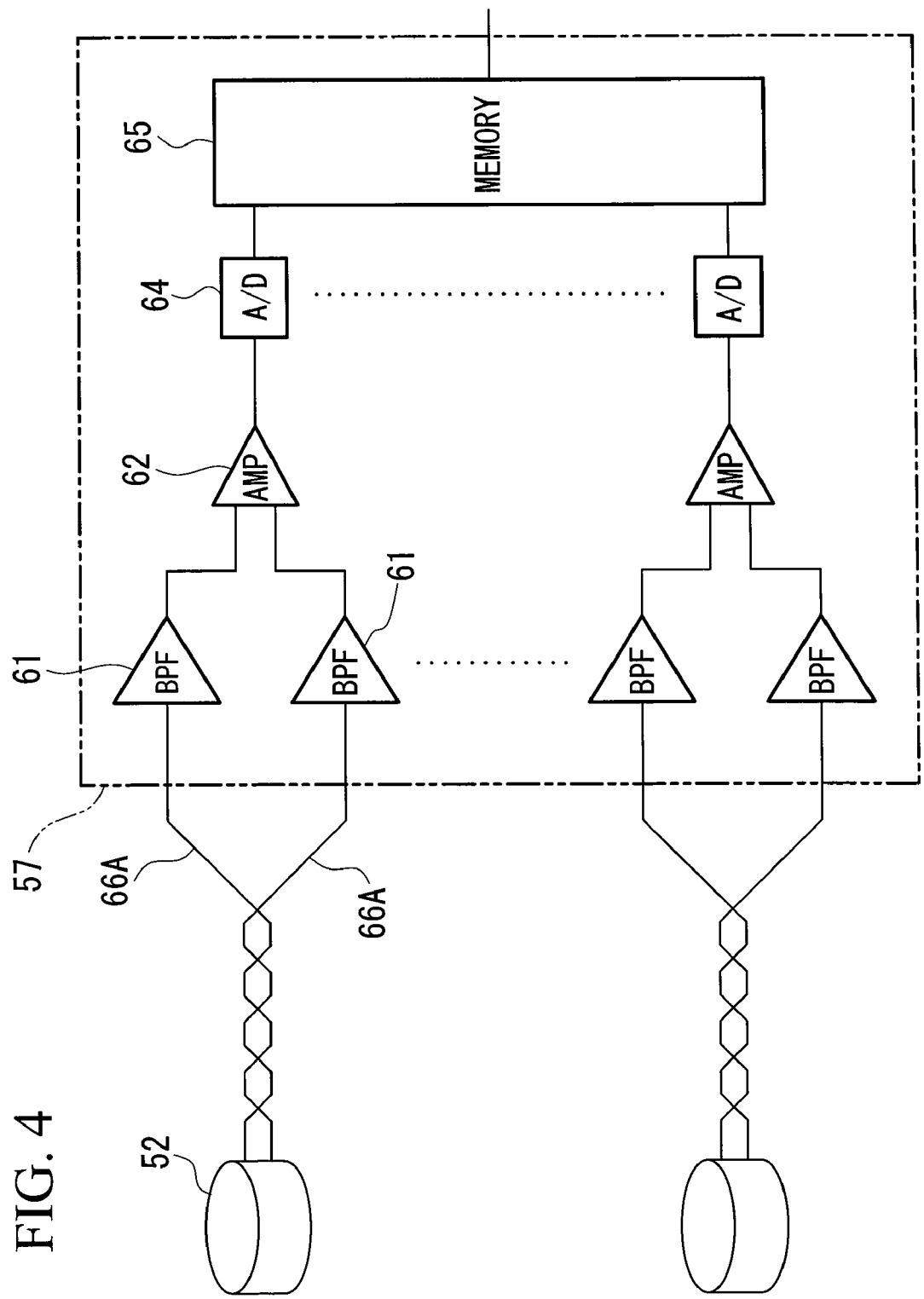
FIG. 4 is a schematic view illustrating the circuitry of a sense-coil receiving circuit shown in FIG. 1.

FIG. 4 is a schematic view illustrating the circuitry of the sense-coil receiving circuit 57 shown in FIG. 1.

As shown in FIG. 4, the sense-coil receiving circuit 57 is formed of band-pass filters (BPF) 61 that remove high-frequency components and low-frequency components containing in the AC voltages including the input position information of the capsule endoscope 20; amplifiers (AMP) 62 that amplify the AC voltages from which the high-frequency components and low-frequency components have been removed; A/D converters 64 that convert the AC voltages to digital signals; and a memory 65 for temporarily storing the digitized amplitude values.

The band-pass filters 61 are disposed in the pair of wires 66A, respectively, that extend from each sense coil 52, and the AC voltages output from the band-pass filters 61 are input to the single amplifier 62. The memory 65 temporarily stores the amplitude values obtained from the nine sense coils 52 and outputs the stored amplitude values to the position detection device 50.

Regarding the waveform of the detected AC voltage, the phase with respect to a waveform applied to the drive coil 51 changes depending on the presence and the position of a magnetic induction coil 42, described below, in the capsule endoscope 20. This phase change may be detected with a lock-in amplifier or the like.

Figure 5:
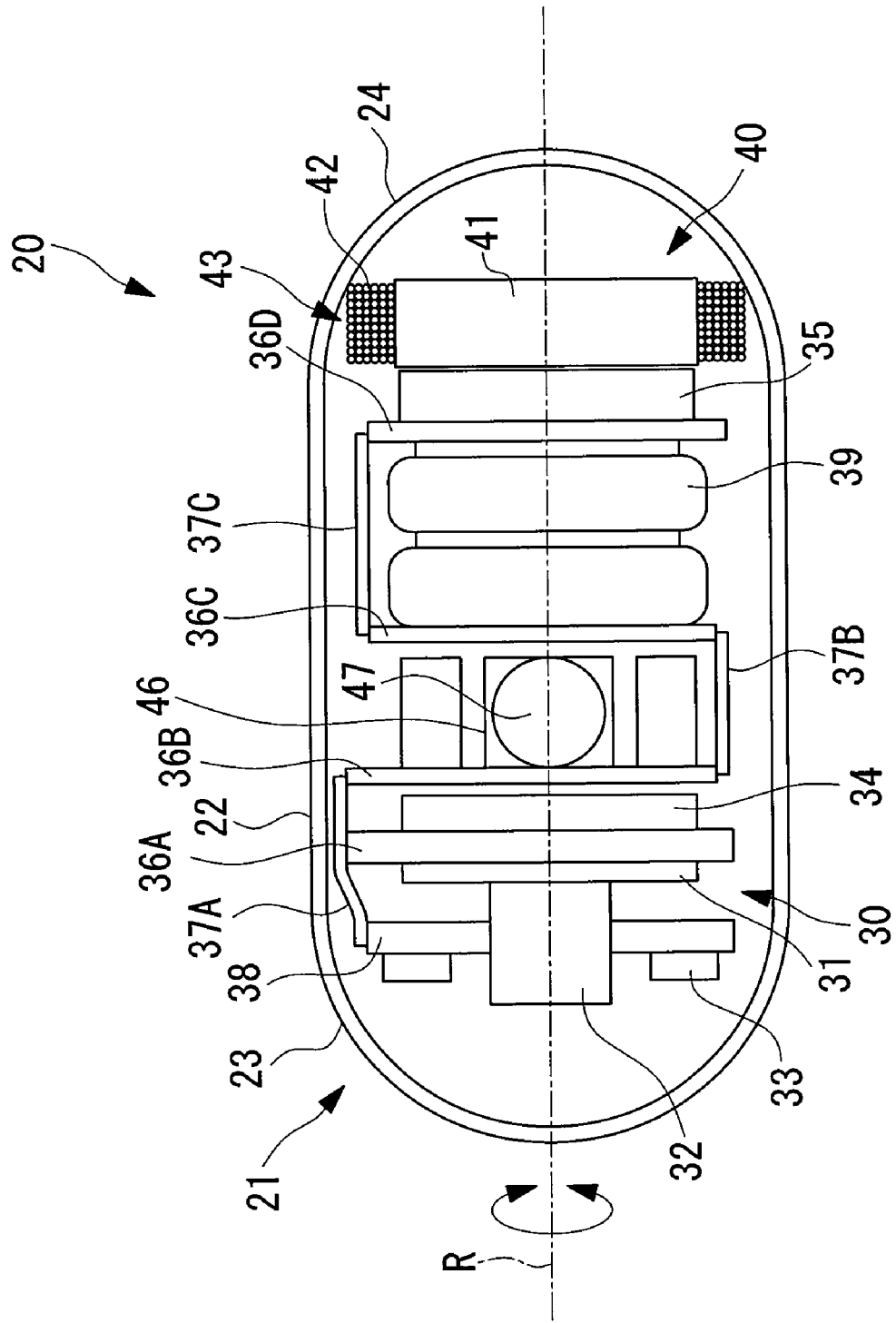
FIG. 5 is a schematic view illustrating the structure of the capsule endoscope system shown in FIG. 1.

FIG. 5 is a schematic view illustrating the structure of the capsule endoscope system shown in FIG. 1.

As shown in FIG. 5, the capsule endoscope 20 is mainly formed of an outer casing 21 that accommodates various devices in the interior thereof; an image-acquisition section 30 that images an internal surface of a passage in the body cavity of the subject; a battery 39 for driving the image-acquisition section 30; and an induced-magnetic-field generating section 40 that generates induced magnetic fields by means of the drive coils 51 described above.

The outer casing 21 is formed of an infrared-transmitting cylindrical capsule main body (hereinafter abbreviated simply as main body) 22 whose central axis defines a rotation axis (longitudinal axis) R of the capsule endoscope 20, a transparent hemispherical front end portion 23 that covers the front end of the main body 22, and a hemispherical rear end portion 24 that covers the rear end of the main body, to form a sealed capsule container with a watertight construction.

The image-acquisition section 30 is mainly formed of a board 36A positioned substantially orthogonal to the rotation axis R; an image sensor 31 disposed on the surface at the front end portion 23 side of the board 36A; a lens group 32 that forms an image of the internal surface of the passage inside the body cavity of the subject on the image sensor 31; an LED (Light Emitting Diode) 33 that illuminates the internal surface of the passage inside the body cavity; a signal processing section 34 disposed on the surface at the rear end portion 24 side of the board 36A; and a wireless element 35 that transmits the image signal to an image display device 80.

The signal processing section 34 is electrically connected to the battery 39 via the board 36A, boards 36B, 36C, and 36D, and flexible boards 37A, 37B, and 37C, is electrically connected to the image sensor 31 via the board 36A, and is electrically connected to the LED 33 via the board 36A, the flexible board 37A, and a support member 38. Also, the signal processing section 34 compresses the image signal that the image sensor 31 acquires, temporarily stores it (memory), and transmits the compressed image signal to the exterior from the wireless element 35, and in addition, it controls the on/off state of the image sensor 31 and the LED 33 based on signals from switch sections 46 to be described later.

The image sensor 31 converts the image formed via the front end portion 23 and the lens group 32 to an electrical signal (image signal) and outputs it to the signal processing section 34. CMOS (Complementary Metal Oxide Semiconductor) devices or CCDs, for example, can be used as this image sensor 31.

Moreover, a plurality of the LEDs 33 are disposed on the support member 38 positioned closer to the front end portion 23 than the board 36A such that gaps are provided therebetween in the circumferential direction around the rotation axis R.

The switch sections 46 are disposed on the board 36B on the rear end portion 24 side of the signal processing section 34. The battery 39 is interposed between the boards 36C and 36D on the rear end portion 24 side of the switch sections 46. The wireless element 35 is disposed on the board 36D on the rear end portion 24 side of the battery 39.

The switch sections 46 have infrared sensors 47, are electrically connected to the signal processing section 34 via the boards 36A and 36B and the flexible board 37A, and are electrically connected to the battery 39 via the boards 36B, 36C, and 36D and the flexible boards 37B and 37C.

Also, a plurality of the switch sections 46 are disposed in the circumferential direction about the rotation axis R at regular intervals, and the infrared sensor 47 is disposed so as to face the outside in the radial direction. In this embodiment, an example has been described in which four switch sections 46 are disposed, but the number of switch sections 46 is not limited to four; any number may be provided.

The induced-magnetic-field generating section 40 is disposed at the rear end portion 24 side of the wireless element

35. The induced-magnetic-field generating section 40 is formed of a core member 41 made of ferrite formed in the shape of a cylinder whose central axis is substantially the same as the rotation axis R; the magnetic induction coil 42 that is disposed at the outer circumferential part of the core member 41; and a capacitor (not shown in the drawing) that is electrically connected to the magnetic induction coil 42. Here, the magnetic induction coil 42 and the capacitor form a LC resonance circuit 43.

In addition to ferrite, materials such as iron, permalloy, nickel, or the like may be used for the core member 41.

Next, the operation of the position detection system 10 having the above-described configuration will be described.

First, the overall operation of the position detection system 10 will be described.

As shown in FIGS. 1 and 2, the capsule endoscope 20 is inserted, per oral or per anus, into a body cavity of a subject 1 who is lying down inside the position detection device 50. The position of the inserted capsule endoscope 20 is detected by the position detection unit 50. The capsule endoscope 20 acquires an image of the internal surface of the passage in the body cavity in the vicinity of the affected area. Then, data for the acquired internal surface of the passage inside the body cavity and data for the vicinity of the affected area are transmitted to an image display device (not shown in the drawings).

Next, the operation of the position detection device 50 characterizing this embodiment will be described.

As shown in FIG. 1, at the position detection device 50, the sine-wave generating circuit 53 generates an AC current on the basis of the output from the position detection device 50, and the AC current is output to the drive-coil driver 54. The frequency of the generated AC current ranges from a few kHz to 100 kHz, and the frequency varies (sweeps) within the above-mentioned range over time, so as to include a resonance frequency to be described later. The sweep range is not limited to the range mentioned above; it may be a narrower range or it may be a wider range, and is not particularly limited.

Instead of constantly performing sweeps, measurement may be carried out by performing an initial sweep to determine a measurement frequency and then fixing the frequency to the measurement frequency. In this way, the measuring speed can be increased. Furthermore, sweeps may be periodically carried out to determine the measurement frequency again. In this way, the measurement can respond to changes in the resonant frequency due to temperature characteristics.

The AC current is amplified in the drive-coil driver 54 based on an instruction from the position detection device 50 and is output to the drive-coil selector 55. The amplified AC current is supplied to the drive coil 51 selected by the position detection device 50 in the drive-coil selector 55. Then, the AC current supplied to the drive coil 51 produces an alternating magnetic field in the operating space of the capsule endoscope 20.

An induced electromotive force generated by the alternating magnetic field causes an induced current to flow in the magnetic induction coil 42 of the capsule endoscope 20, which is positioned in the alternating magnetic field. When an induced current flows in the magnetic induction coil 42, an induced magnetic field is formed by the induced current.

Since the magnetic induction coil 42 forms the LC resonance circuit 43 together with the capacitor, if the cycle of the alternating magnetic field matches the resonant frequency of the LC resonance circuit 43, the induced current flowing in LC resonance circuit 43 (magnetic inductance coil 42) increases and the induced magnetic field that is formed becomes more intense. Furthermore, since a core member 41 formed of dielectric ferrite is disposed at the center of the magnetic induction coil 42, the induced magnetic field can be easily concentrated at the core member 41, and the induced magnetic field formed becomes even more intense. Dielectric ferrite may be substituted by a magnetic material, such as iron, nickel, or cobalt and, alloys of such magnetic materials and ferrite may also be used.

The induced magnetic field generates an induced electromotive force in the sense coils 52, and an AC voltage (magnetic information) containing position information of the capsule endoscope 20 is generated at the sense coils 52. This AC voltage is input the sense-coil receiving circuit 57 via the sense-coil selector 56 and is converted to a digital signal.

As shown in FIG. 4, high-frequency components and low-frequency components of the AC voltage input to the sense-coil receiving circuit 57 are removed by the band-pass filters 61, and then the AC voltage is amplified by the amplifier 62. Such an AC voltage from which unwanted components are removed is converted to a digital signal at the A/D converter 64 and is stored in the memory 65.

The memory 65 stores amplitude values corresponding to, for example, one sweep cycle in which a sine-wave signal generated in the sine-wave generating circuit 53 is swept near the resonance frequency of the LC resonance circuit 43 and outputs the amplitude values of one cycle, as a group, to the position detection device 50.

Figure 6:
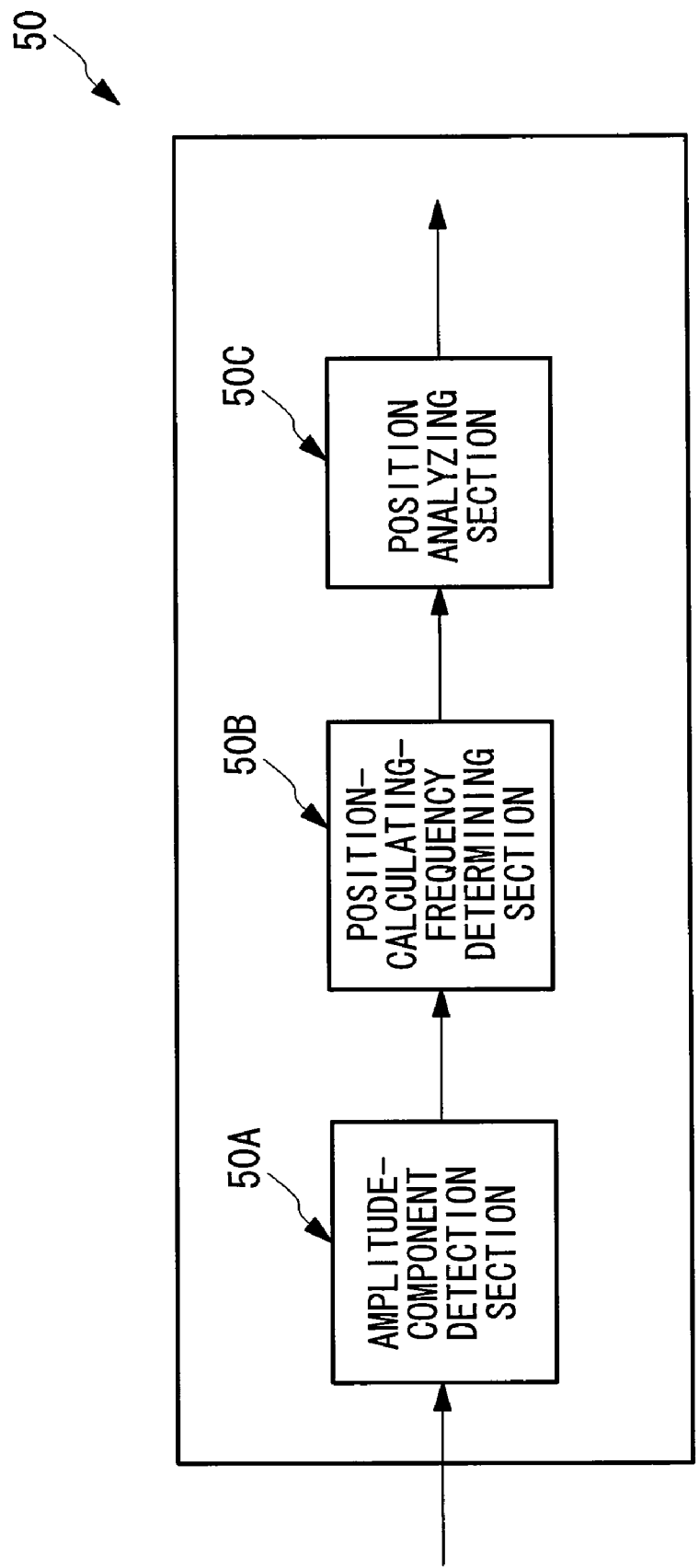
FIG. 6 is a block diagram illustrating, in outline, the position detection system shown in FIG. 1.

FIG. 6 is a block diagram illustrating, in outline, the position detection device 50 shown in FIG. 1. As shown in FIG. 6, the AC voltage input to the position detection device 50 is input to the amplitude-component detection section 50A. From the alternating magnetic field, the amplitude-component detection section 50A separates the real part of the AC voltage having the same phase as that of the alternating magnetic field and the imaginary part of an AC voltage orthogonal to the alternating magnetic field. At least one of the real part and the imaginary part of the separated AC voltage is input from the amplitude-component detection section 50A to the position-calculating-frequency determining section S0B and the position analyzing section S0C.

Fourier transformation is used to separate the real part and the imaginary part of the alternating magnetic field at the amplitude-component detection section 50A. The timing for starting the Fourier transformation is controlled so that its difference with respect to the phase of the alternating magnetic field generated in the drive coils 51 is maintained at a constant relative relationship. By separating the real part and the imaginary part of the alternating magnetic field using Fourier transformation, at least one of the real part and the imaginary part can be detected more quickly and accurately. Furthermore, by maintaining a constant relative relationship between the timing for starting the Fourier transformation and the phase of the alternating magnetic field, at least one of the real part and the imaginary part can be detected more accurately.

Instead of using Fourier transformation, the amplitude-component detection section 50A may be provided with at least one of a phase detector and a lock-in amplifier. Since at least one of the phase detector and the lock-in amplifier is provided in the amplitude-component detection section 50A, the amplitude-component detection section 50A can easily detect at least one of the real part and the imaginary part of the alternating magnetic field from the outputs of the magnetic-field sensors acquired by the plurality of sense coils 52.

Figure 7:
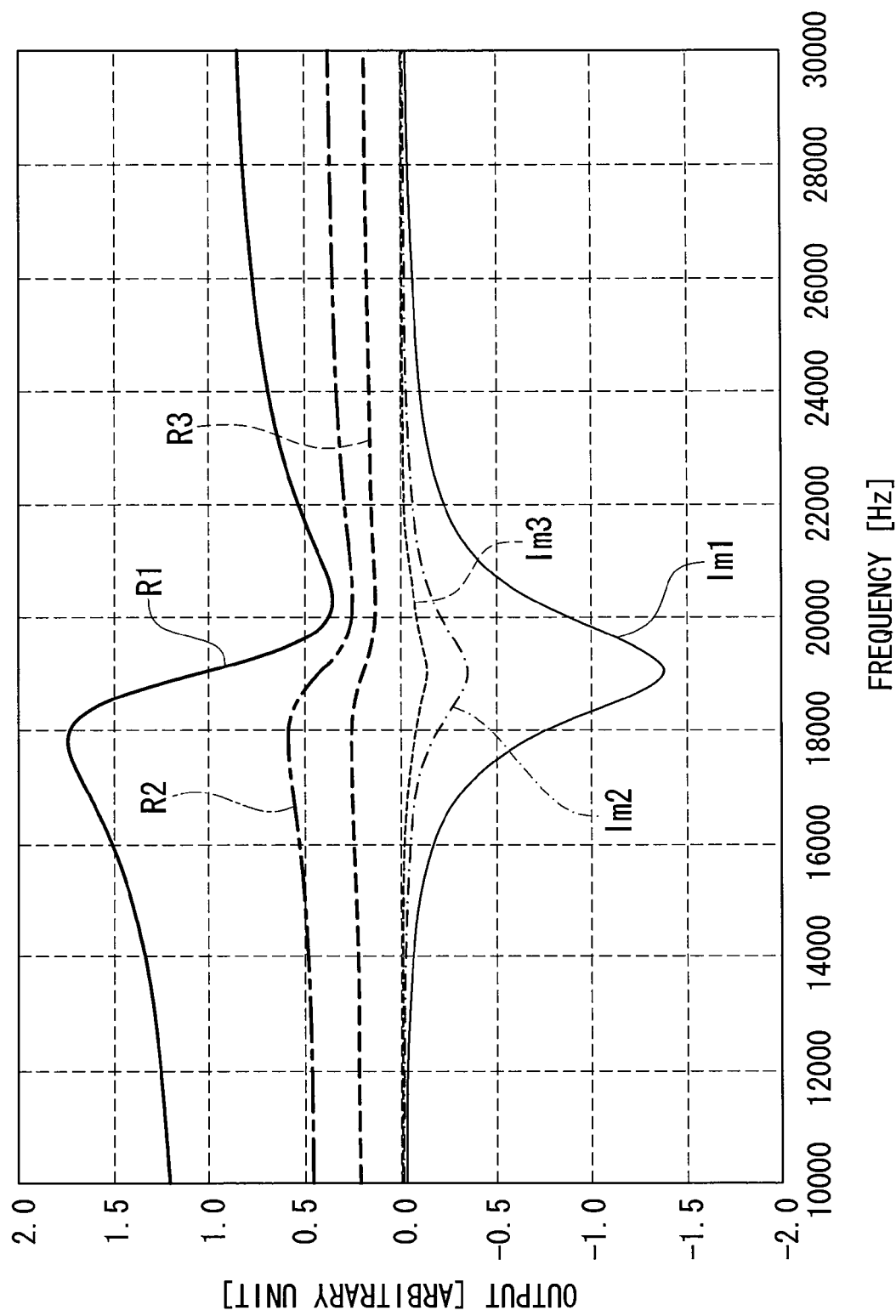
FIG. 7 illustrates the relationship between a real part and an imaginary part of an AC voltage separated by an amplitude-component detecting section shown in FIG. 6.

FIG. 7 illustrates the relationship between the real part and the imaginary part of an AC voltage separated by the amplitude-component detection section 50A. In FIG. 7, the horizontal axis represents the frequency of the alternating magnetic field, and the vertical axis represents the changes in gain (dBm) and the phase change (degree) of the AC voltage flowing through the LC resonance circuit 43.

Figure 8:
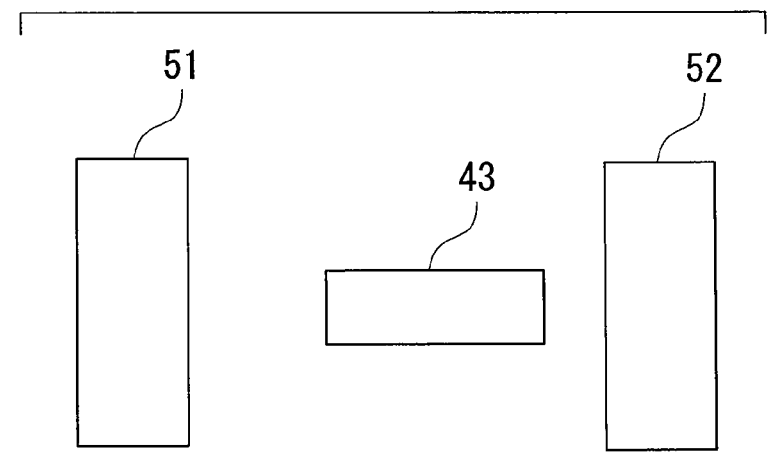
FIG. 8 the relative positional relationship of drive coils, an LC resonant circuit, and a sense coil shown in FIG. 7.
Figure 9:
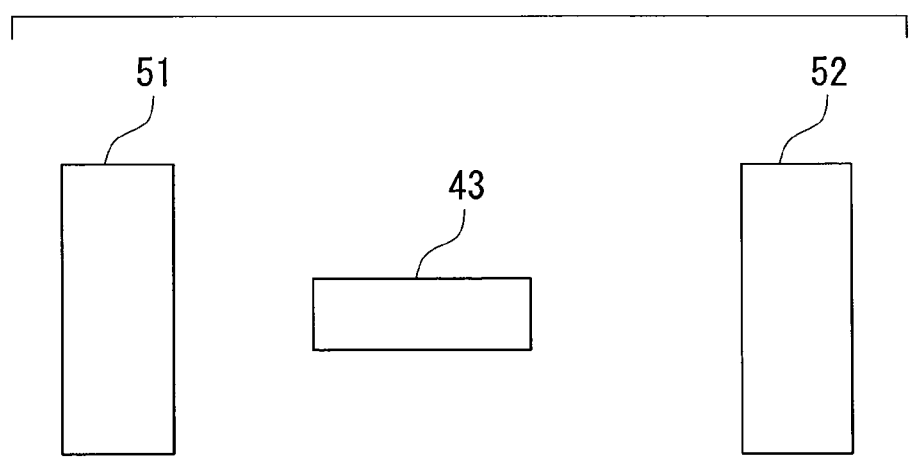
FIG. 9 illustrates the relative positional relationship of drive coils, an LC resonant circuit, and a sense coil shown in FIG. 7.
Figure 10:
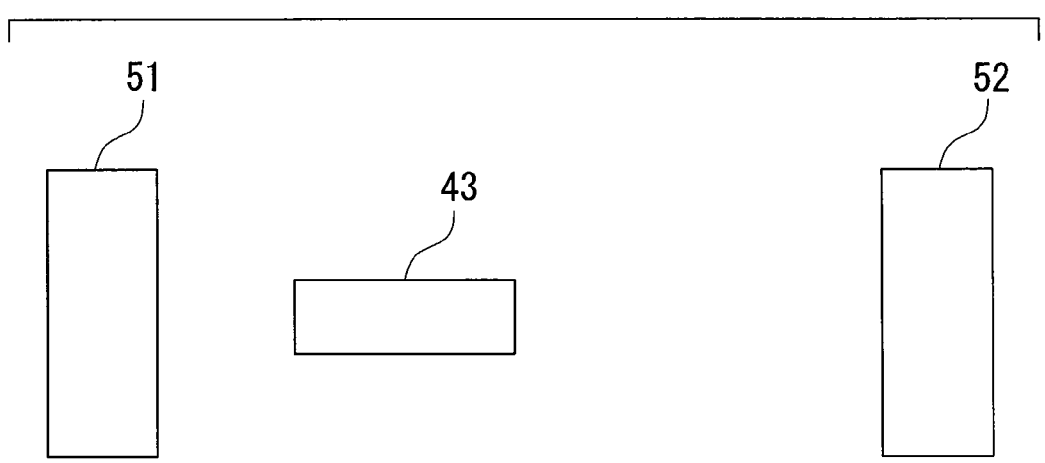
FIG. 10 illustrates the relative positional relationship of drive coils, an LC resonant circuit, and a sense coil shown in FIG. 7.

FIGS. 8, 9, and 10 illustrate the relative positional relationship of the drive coils 51, the LC resonance circuit 43, and the sense coils 52 in FIG. 7.

In FIG. 7, output-value curves R1, R2, and R3 of the real part and output-value curves Im1, Im2, and Im3 of the imaginary part of the AC voltage are the output-value curves of the real part and the output-value curves of the imaginary part when the relative positional relationships of the drive coils 51, the LC resonance circuit 43, and the sense coils 52 are configured as shown in FIGS. 8, 9, and 10, respectively.

The output-value curves R1, R2, and R3 of the real part are offset to the larger output side with respect to the distances from the drive coils 51 to the LC resonance circuit 43 and to the sense coils 52, and their values are maximized and minimized near the resonant frequency. The difference between the maximum value and minimum value changes depending on the distances from the drive coils 51 to the LC resonance circuit 43 and the sense coils 52.

The output-value curves Im1, Im2, and Im3 of the imaginary part are not offset, regardless of the distances between the drive coils 51 and the LC resonance circuit 43, and the drive coils 51 and the sense coils 52. The output-value curves Im1, Im2, and Im3 of the imaginary part are minimized at the resonant frequency, and the amplitudes change depending on the distance between the drive coils 51 and the LC resonance circuit 43, and the distance from the drive coils 51 to the sense coils 52.

The position-calculating-frequency determining section 50B detects the minimum values of the output-value curves Im1, Im2, and Im3 of the imaginary part of the input AC voltage in order to detect the resonant frequency at the LC resonance circuit 43 and sets the resonant frequency as a position-calculating frequency.

The position analyzing section 50C detects the amplitude values of the resonant frequencies of the output-value curves Im1, Im2, and Im3 of the imaginary part input from the sense coils 52 and calculates and estimates the position and orientation of the LC resonance circuit 43 (capsule endoscope 20) on the basis of the detected amplitude values.

Instead, the frequencies at which the output-value curves R1, R2, and R3 of the real part of the input AC voltage have the maximum values and the minimum values may be detected at the position-calculating-frequency determining section SOB, and the detected frequencies may be set as a position-calculating frequencies. In this case, the position analyzing section 50C detects the amplitude values of the output-value curves R1, R2, and R3 input from the sense coils 52 at the position-calculating frequency and calculates and estimates the position and the orientation of the LC resonance circuit 43 (capsule endoscope 20) on the basis of the detected amplitude values.

Subsequently, when the position and so on of the capsule endoscope 20 is estimated, the position and so on of the capsule endoscope 20 is estimated at the position-calculating frequency set by the above-described position-calculating-frequency determining section SOB. More specifically, an AC current with the position-calculating frequency is supplied to the drive coils 51 to generate an alternating magnetic field at that frequency in order to estimate the position and so on of the capsule endoscope 20.

According to the above-described position detection system 10, the amplitude-component detection section 50A detects at least one of the amplitude component whose phase is substantially orthogonal to the alternating magnetic field and the amplitude component whose phase is substantially the same as that of the alternating magnetic field, and the position analyzing section 50C can calculate the position and so on of the capsule endoscope 20 on the basis of the amplitude component.

In other words, the amplitude-component detection section 50A can separate amplitude components that include only information associated with the position and so on of the capsule endoscope 20 and do not include information associated with the position and so on of the drive coils 51 from the output of the sense coils 52 that has received the magnetic field formed by the drive coils 51 and the LC resonance circuit 43. Therefore, at least one of the position and the orientation of the capsule endoscope 20 can be calculated without performing calibration measurement.

Since the LC resonance circuit 43 generates an induced magnetic field from the alternating magnetic field, a power source does not have to be added to the LC resonance circuit 43. Thus, the number of components installed in the capsule endoscope 20 can be reduced. Since an induced magnetic field used for position detection of the capsule endoscope 20 is generated, a power source installed inside the capsule endoscope 20 is not used. Therefore, the life of the capsule endoscope 20 is not affected by the life of such a power source.

As described above, when determining the frequency (position-calculating frequency) of the alternating magnetic field used for calculating at least one of the position and the orientation of the capsule endoscope 20, the position-calculating frequency may be determined by sweeping the frequency of the alternating magnetic field while determining the position and the orientation of the capsule endoscope 20, the position-calculating frequency may be determined in advance before measuring the position and the orientation, or the position-calculating frequency determined in advance may be printed on the capsule endoscope 20 and then the printed position-calculating frequency may be used.

In this way, the frequency of the alternating magnetic field does not have to be swept in a frequency band including the position-calculating frequency in order for the position-calculating-frequency determining section 50B to obtain a resonant frequency in advance, and thus the amount of time required for calculating at least one of the position and the orientation of the device can be reduced.

As described above, after the position-calculating frequency used for one capsule endoscope 20 is determined, that position-calculating frequency may be continuously used, or when a change in the resonant frequency is detected through monitoring the resonant frequency of the LC resonance circuit 43, a new position-calculating frequency may be determined on the basis of the changed resonant frequency.

In this way, for example, even when the resonant frequency changes due to a change in the temperature of the magnetic induction coil 42, the change in the resonant frequency can be detected by the position-calculating-frequency determining section 50B, and at least one of the position and the orientation of the device can always be calculated at the resonant frequency. Therefore, the accuracy of calculating the position and the orientation of the device can be maintained.

Second Embodiment

Next, a second embodiment of the present invention will be described with reference to FIGS. 11 to 13.

The basic structure of a position detection system according to this embodiment is the same as that according to the first embodiment, except that the structure of the position detection device differs from that according to the first embodiment. Therefore, in this embodiment, only the position detection device and its periphery will be described with reference to FIGS. 11 to 13, and a description of the capsule endoscope and so on will be omitted here.

Figure 11:
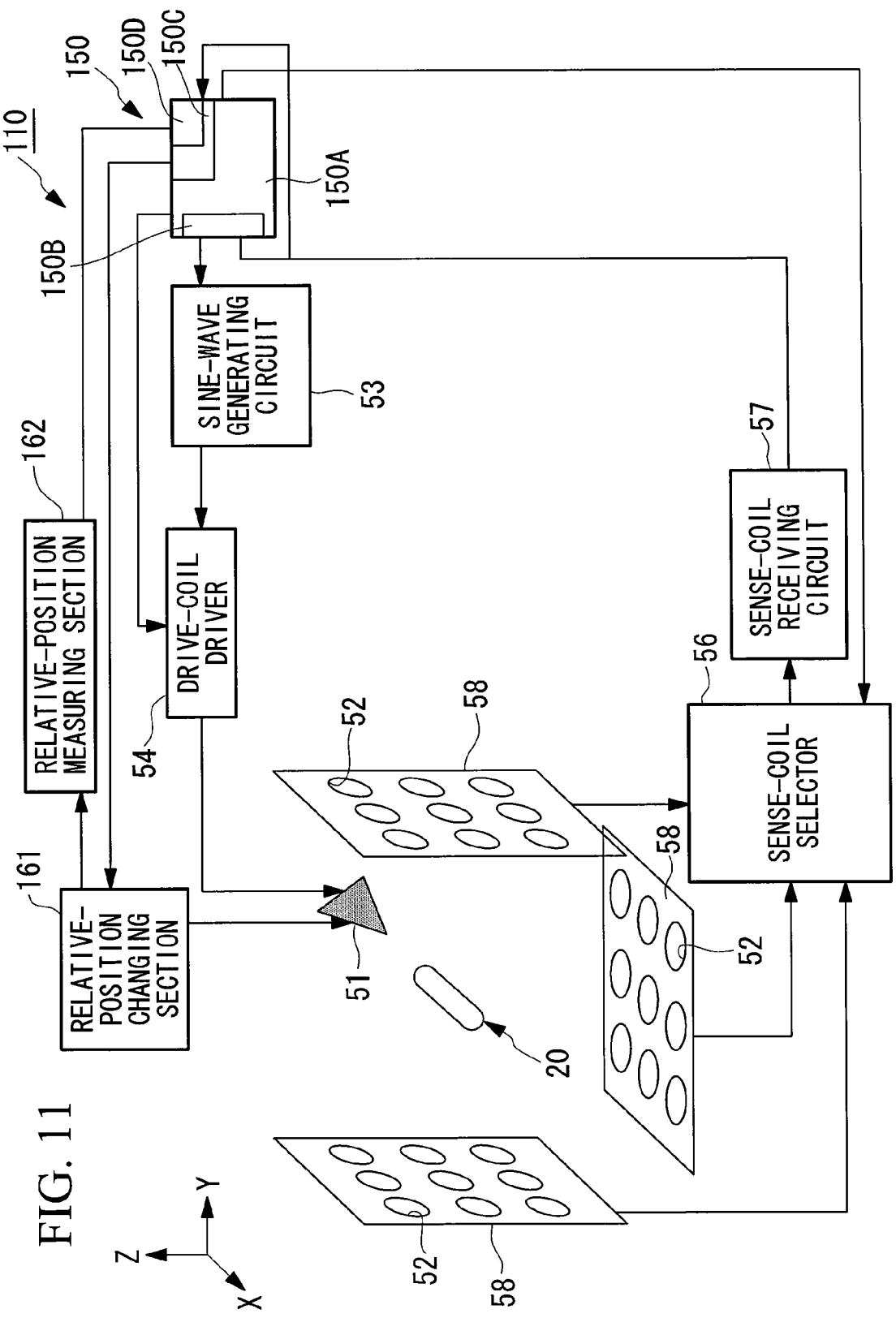
FIG. 11 is a block diagram illustrating, in outline, a position detection system according to a second embodiment of the present invention.

FIG. 11 is a block diagram illustrating, in outline, the position detection system according to this embodiment.

Components that are the same as those according to the first embodiment will be represented by the same reference numerals, and descriptions thereof will be omitted here.

As shown in FIG. 11, a position detection system 110 is mainly formed of a capsule endoscope 20 that optically images an internal surface of a passage in the body cavity and wirelessly transmits an image signal and a position detection device (amplitude-component detection section, position-calculating-frequency determining section, position analyzing section, drive-coil driver) 150 that detects the position of the capsule endoscope 20.

As shown in FIG. 11, the position detection device 150 is electrically connected to a drive coil 51 that generate an induced magnetic field at magnetic inductance coils, described below, in the capsule endoscope 20, sense coils 52 that detect the induced magnetic field generated at the magnetic inductance coils, a relative-position changing section 161 that changes the relative position of the drive coil 51 and the sense coils 52, and a relative-position measuring section 162 that measures the relative position.

The position detection device 150 calculates the position and so on of the capsule endoscope 20 on the basis of the induced magnetic field detected by the sense coils 52 and controls the alternating magnetic field formed by the drive coil 51.

Between the position detection device 150 and the drive coil 51 there are provided a signal generating circuit 53 that generates an AC current based on the output from the position detection device 150 and a drive-coil driver 54 that amplifies the AC current input from the signal generating circuit 53 based on the output from the position detection device 150.

Between the position detection device 150 and the drive coil 51 there is provided the relative-position changing section 161, and between the relative-position changing section 161 and the position detection device 150 there is provided the relative-position measuring section 162. The output of the position detection device 150 is input to a drive coil unit, to be described later, via the relative-position changing section 161. Information about the relative positions of the drive coil 51 and the sense coils 52 is acquired by the relative-position measuring section 162 from the drive coil unit via the relative-position changing section 161, and the acquired information is input to the position detection device 150.

Figure 12:
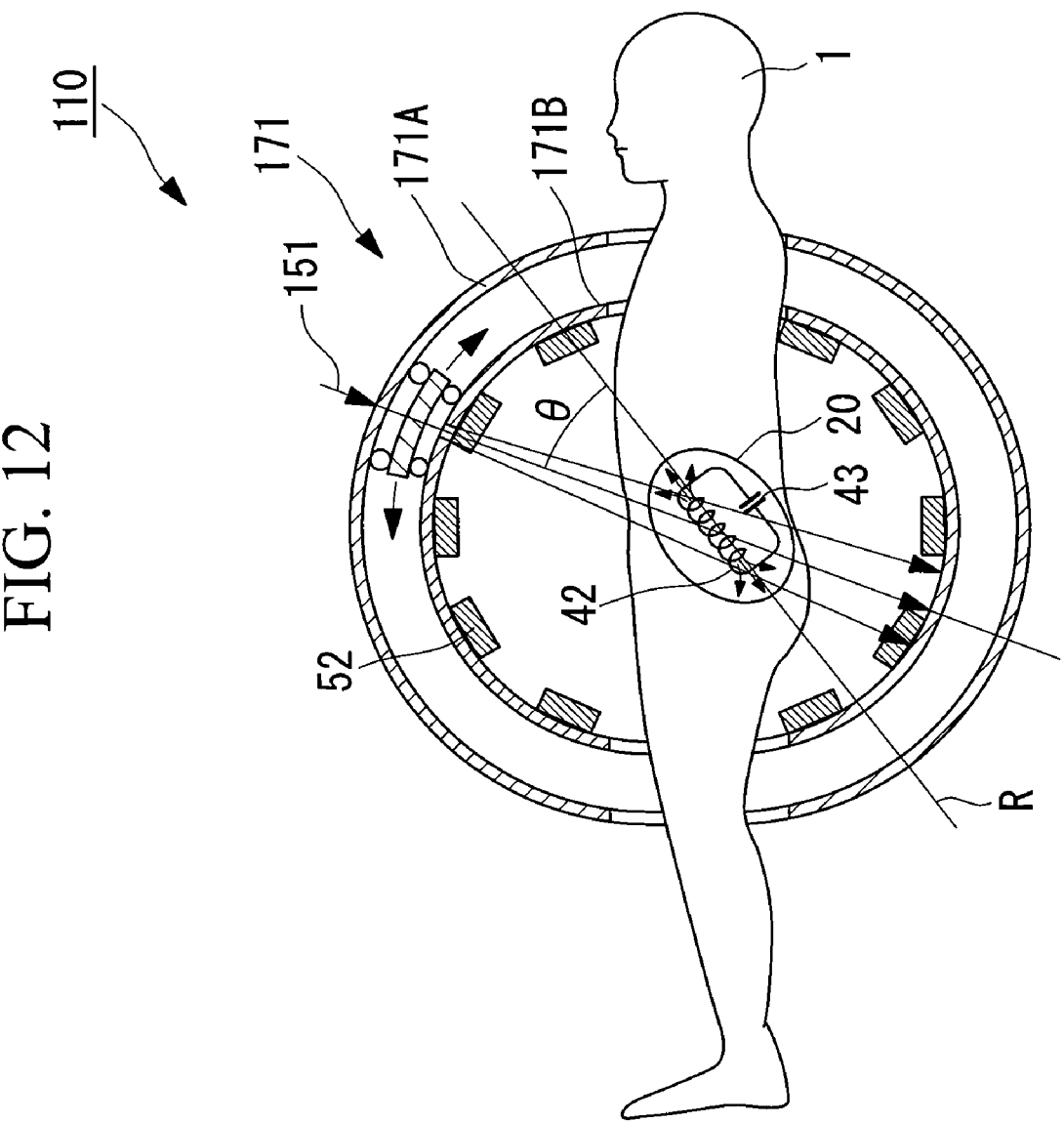
FIG. 12 illustrates the positional relationship between a drive coil unit including drive coils shown in FIG. 11 and sense coils.

FIG. 12 illustrates the positional relationship between the drive coil unit, including the drive coil 51 shown in FIG. 11, and the sense coils 52.

In the position detection device 150, there are provided a frame member 171 composed of a substantially spherical outer frame 171A and inner frame 171B, a drive coil unit 151 arranged movably between the outer frame 171A and the inner frame 171B, and the sense coils 52 arranged on the inner surface of the inner frame 171B, as shown in FIG. 12.

Figure 13:
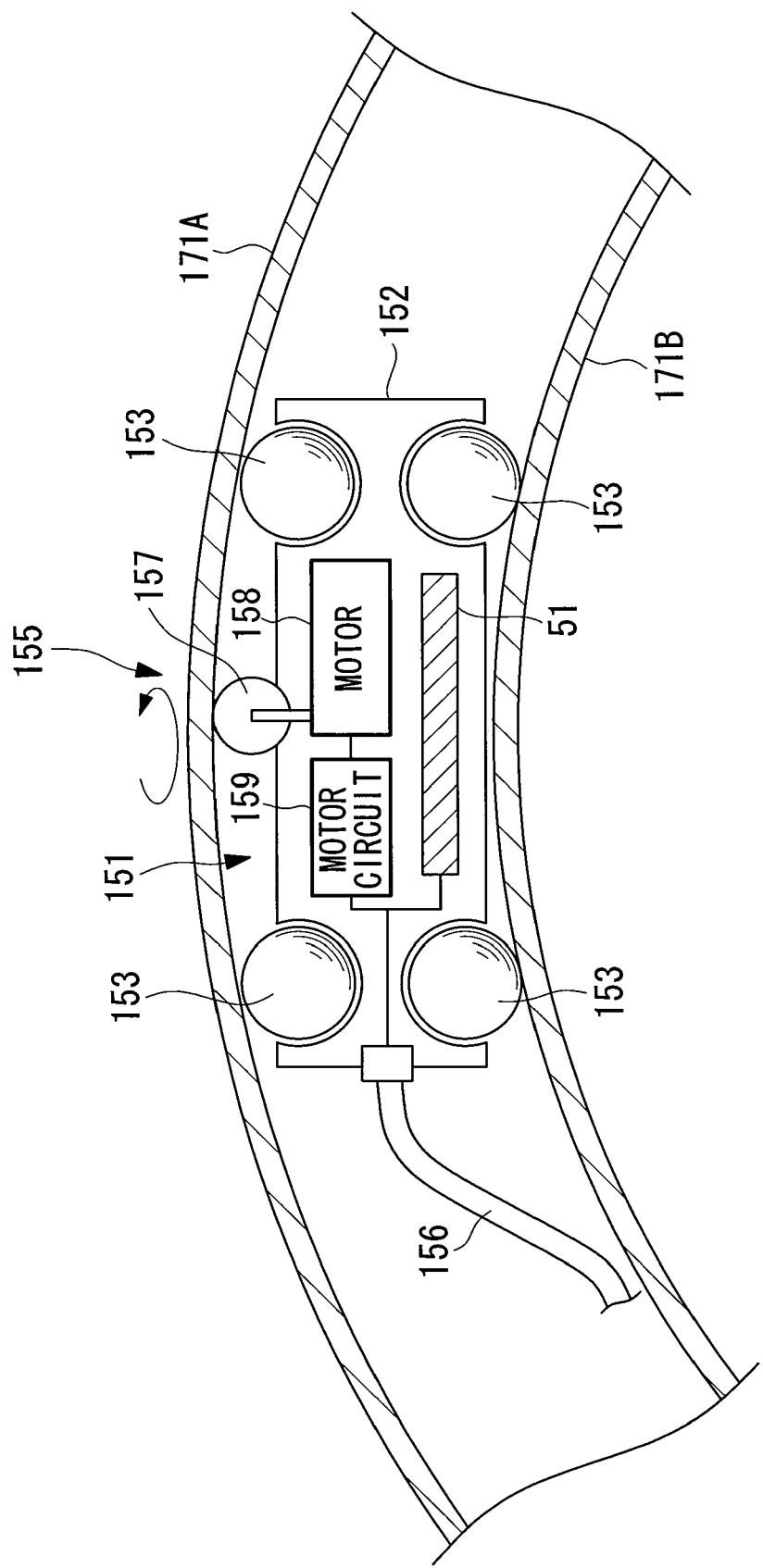
FIG. 13 illustrates, in outline, the structure of the drive coil unit shown in FIG. 12.

FIG. 13 illustrates, in outline, the structure of the drive coil unit 151 shown in FIG. 12.

As shown in FIG. 13, the drive coil unit 151 is mainly composed of a substantially rectangular casing 152; spherical sections 153 arranged in four corners of the surfaces of the casing 152 that face the outer frame 171A and the inner frame 171B; the drive coil 51; a direction changing section 155 for controlling the direction of movement of the drive coil unit 151; and a cord-like connection member 156 for electrically connecting the drive coil unit 151, the drive-coil driver 54, and the relative-position changing section 161.

The direction changing section 155 is mainly composed of a driving body 157 arranged on a surface facing the outer frame 171A so as to protrude from the surface, a motor 158 for controlling the rotation of the driving body 157, and a motor circuit 159 for controlling the driving of the motor 158.

The method of detecting the position and so on of the capsule endoscope 20 for the position detection system 110 with the above-described structure is the same as that in the first embodiment, and thus a description thereof will be omitted here.

The position detection device 150 outputs a signal for changing the position of the drive coil unit 151 to the relative-position changing section 161 when the amplitude of the AC voltage output from the sense coils 52 becomes small. The relative-position changing section 161 outputs a control signal to the direction changing section 155 to move the drive coil unit 151 in a predetermined direction.

In the above-described position detection system 110, since the drive coil 51 and the sense coils 52 are provided as separate bodies and the drive coil 51 is installed in the drive coil unit 151, the drive coil 51 and the sense coils 52 can be moved separately.

The position detection device 150 moves the drive coil 51 on the basis of the output from the sense coils 52, which changes in accordance with the relative position of the drive coil 51 and the LC resonance circuit 43, and can control the drive coil 51 and the sense coils 52 to establish a suitable relative positional relationship.

More specifically, the position detection device 150 moves the drive coil 51 to a position where the induced magnetic field generated at the LC resonance circuit 43 is maximized, i.e., a position where the direction of the center axis of the magnetic induction coil 42 and the direction of the magnetic flux of the alternating magnetic field entering the magnetic induction coil 42 substantially match.

By moving the drive coil 51, the relative positional relationship between the drive coil 51 and the amplifier 62 changes, and the alternating magnetic field that directly enters the sense coils 52 from the drive coil 51 changes. In this embodiment, the amplitude-component detection section provided in the position detection device 150 separates the imaginary part (amplitude component) of the AC voltage to detect an amplitude component. Therefore, even when the alternating magnetic field changes, the position and so on of the capsule endoscope 20 can be estimated without performing calibration measurement.

As described above, the position detection device 150 may control the position of the drive coil 51 to change the direction of the alternating magnetic field generated by the drive coil 51, to change the intensity of the alternating magnetic field, or to change the direction and the intensity of the alternating magnetic field.

In this way, the drive coil 51 and the LC resonance circuit 43 can be prevented from being disposed in positions that make it difficult to generate an induced magnetic field at the LC resonance circuit 43.

As described above, the drive coil 51 may be provided in the drive coil unit 151 and moved, or a plurality of drive coils 51 may be fixed and a drive coil 51 to be driven selected.

In this way, the same effect as moving the drive coil 51 can be achieved without actually moving the drive coil 51.

As described above, the drive coil 51 may move relative to the LC resonance circuit 43, or the sense coils 52 may move relative to the LC resonance circuit 43.

In this way, the induced magnetic field generated at the LC resonance circuit 43 can be detected more efficiently by the sense coils 52.

Figure 14:
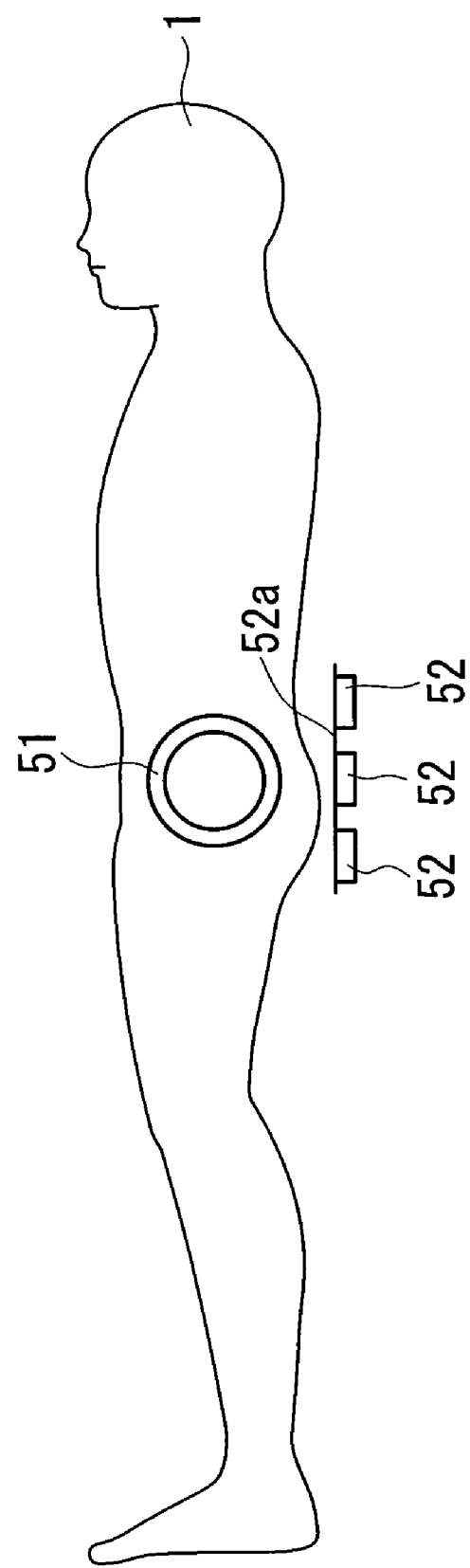
FIG. 14 illustrates another arrangement of a drive coil and the sense coils.

FIG. 14 illustrates another arrangement of the drive coil and the sense coils.

In this embodiment, the sense coils 52 are fixed to the inner frame 171B, as described above, to detect the induced magnetic field generated at the LC resonance circuit 43. However, as shown in FIG. 14, the sense coils 52 may be fixed to a fixing member 52a that is fixed to the subject 1 and the drive coil 51 may also be fixed to the subject 1. Here, the sense coils 52 and the drive coil 51 are provided as separate bodies.

According to such a structure, for example, if the subject 1 moves and thus the positional relationship between the sense coils 52 and the drive coil 51 changes, the position and so on of the capsule endoscope 20 can be continuously detected because calibration is not required. Moreover, the sense coils 52 and the drive coil 51 can be attached to the subject without causing any discomfort to detect the position and so on of the capsule endoscope 20.

Third Embodiment

Next, a third embodiment of the present invention will be described with reference to FIGS. 15 to 18C.

The basic structure of a position detection system according to this embodiment is the same as that according to the first embodiment, except that a magnetic guidance device is added to the position detection system. Therefore, in this embodiment, only the magnetic guidance device and its periphery will be described with reference to FIGS. 15 to 18C, and a detailed description of the position detection system and so on will be omitted here.

Figure 15:
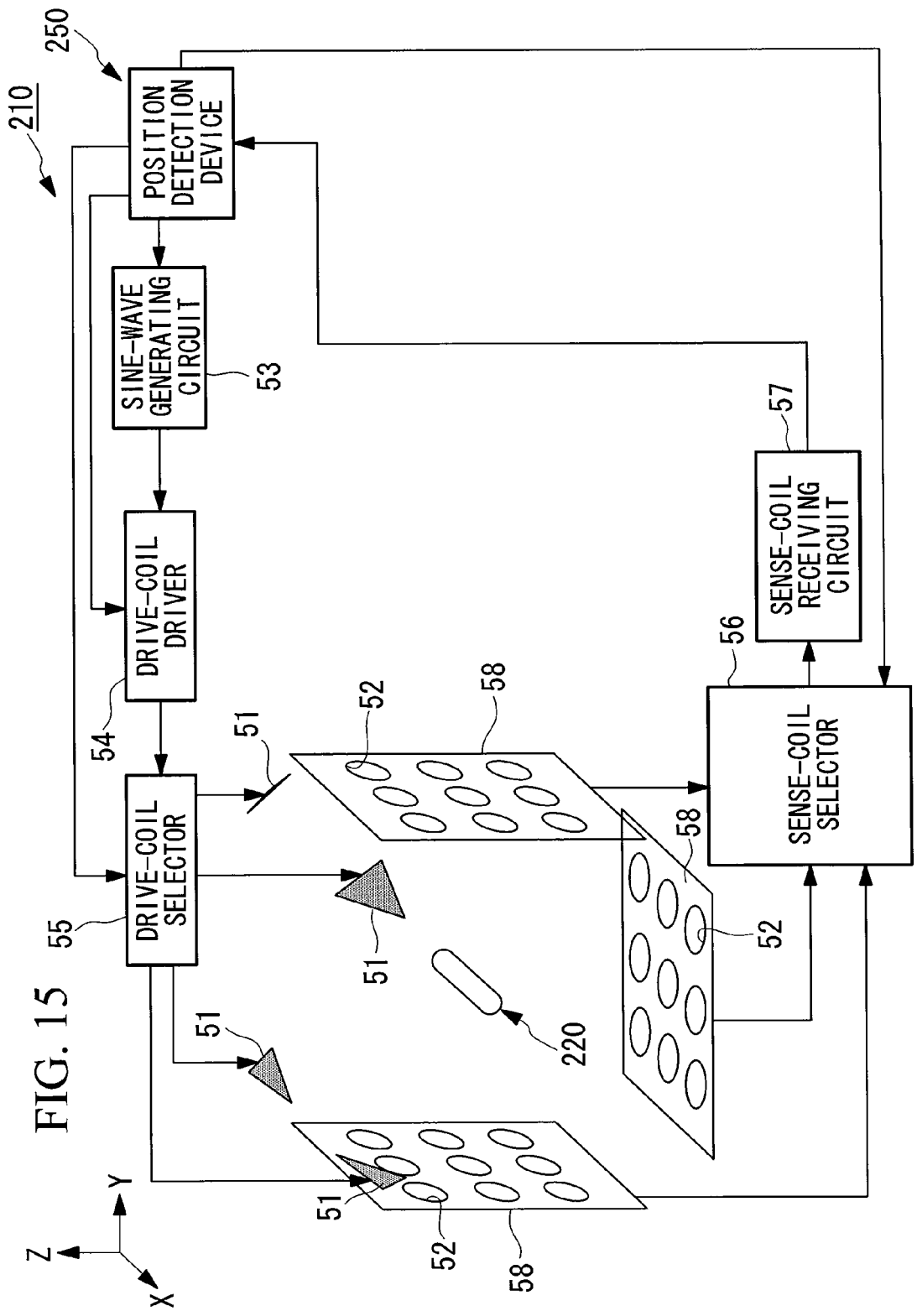
FIG. 15 is a block diagram illustrating, in outline, a position detection system according to a third embodiment of the present invention.
Figure 16:
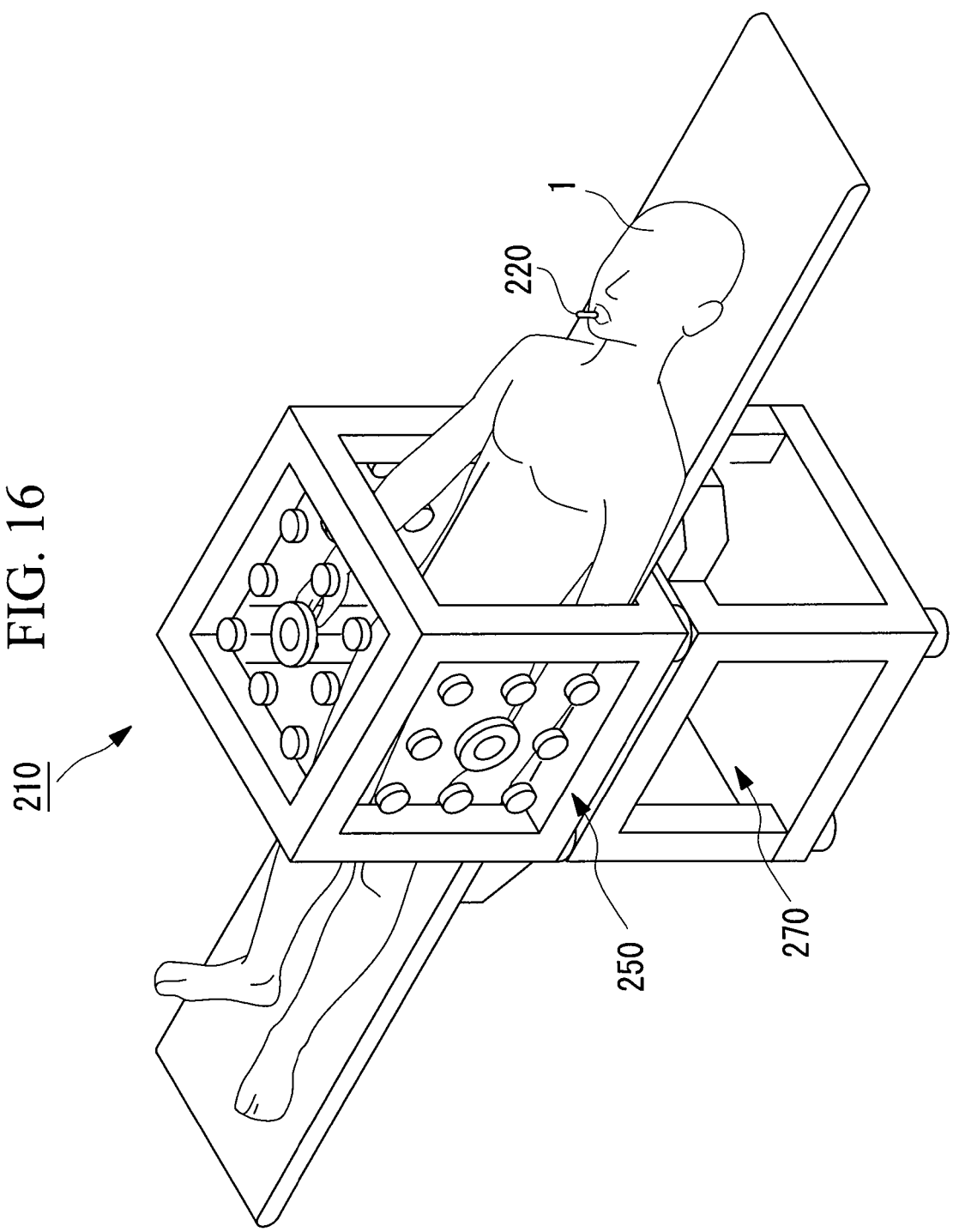
FIG. 16 is a schematic view illustrating the structure of the position detection system shown in FIG. 15.
Figure 17:
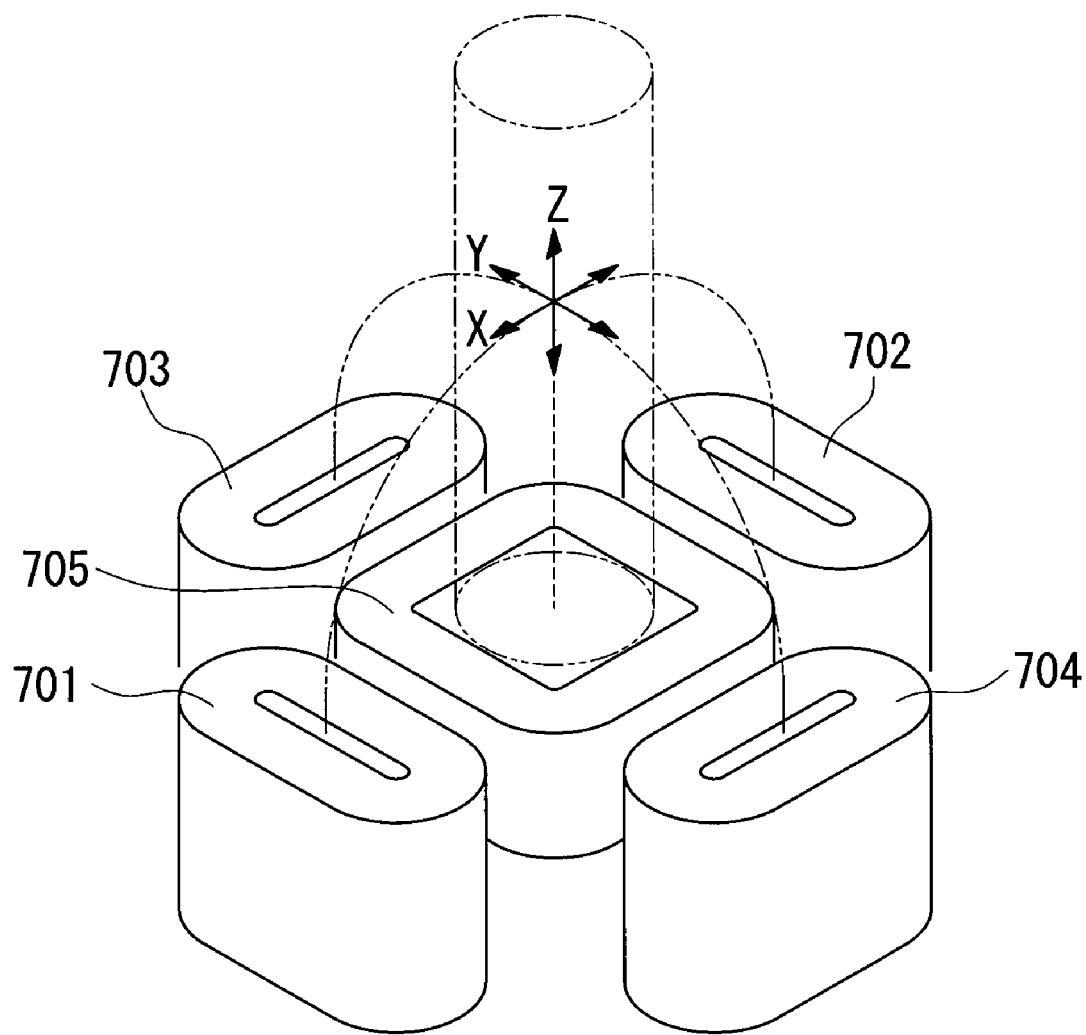
FIG. 17 is a schematic view illustrating a magnetic induction device shown in FIG. 15.

FIG. 15 is a block diagram illustrating, in outline, the position detection system according to this embodiment. FIG. 16 is a schematic view illustrating the structure of the position detection system shown in FIG. 15. FIG. 17 is a schematic view illustrating the magnetic induction device shown in FIG. 15.

Components that are the same as those according to the first embodiment will be represented by the same reference numerals, and descriptions thereof will be omitted here.

As shown in FIGS. 15 to 17, a position detection system 210 is mainly formed of a capsule endoscope 220 that optically images an internal surface of a passage in the body cavity and wirelessly transmits an image signal, a position detection device 250 (amplitude-component detection section, position-calculating-frequency determining section, position analyzing section, drive-coil driver) that detects the position of the capsule endoscope 220, and a magnetic guidance device 270 that guides the capsule endoscope 220.

Figure 18B:
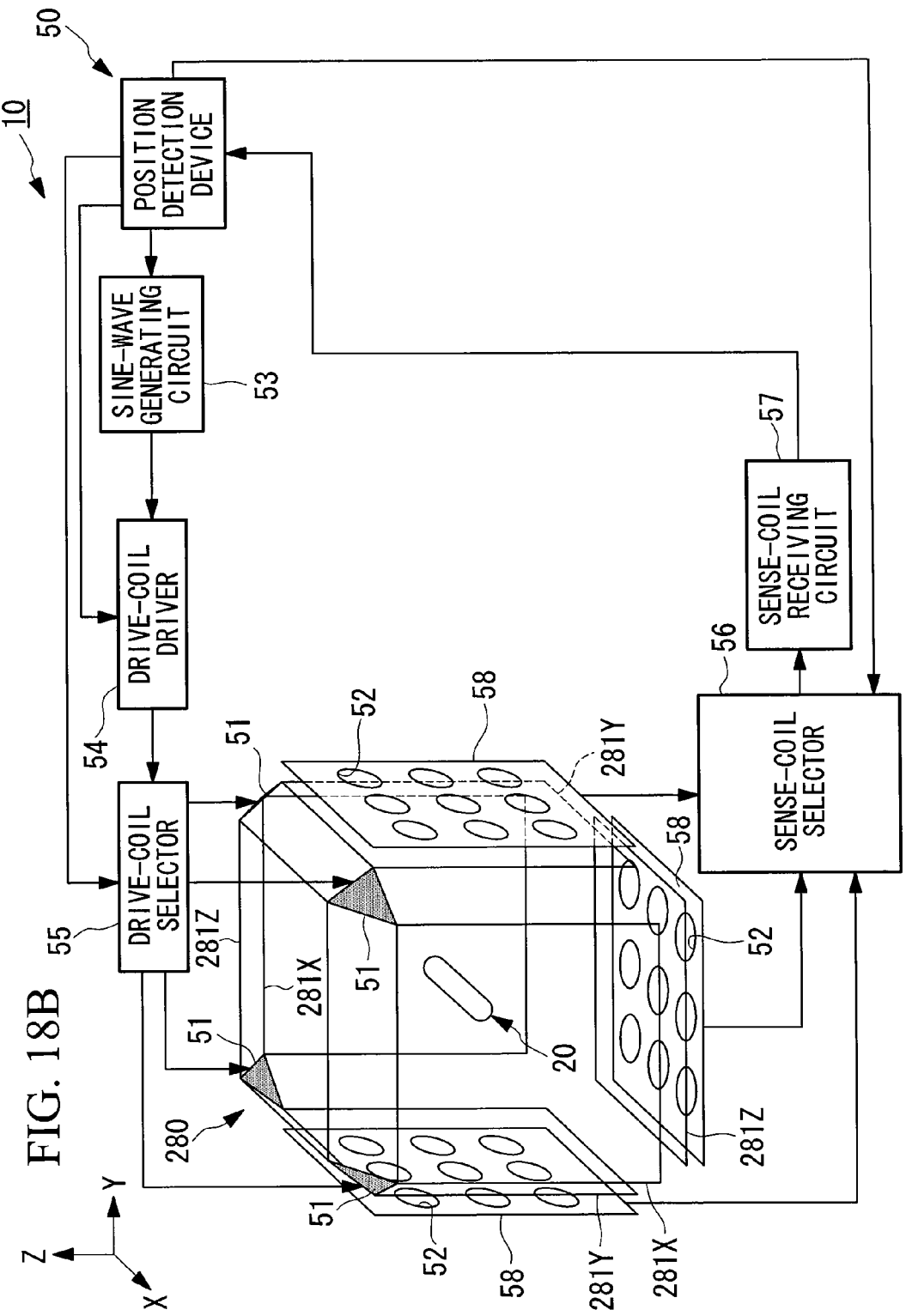
FIG. 18B is a schematic view illustrating the entire structure of the position detection system shown in FIG. 15.
Figure 18C:
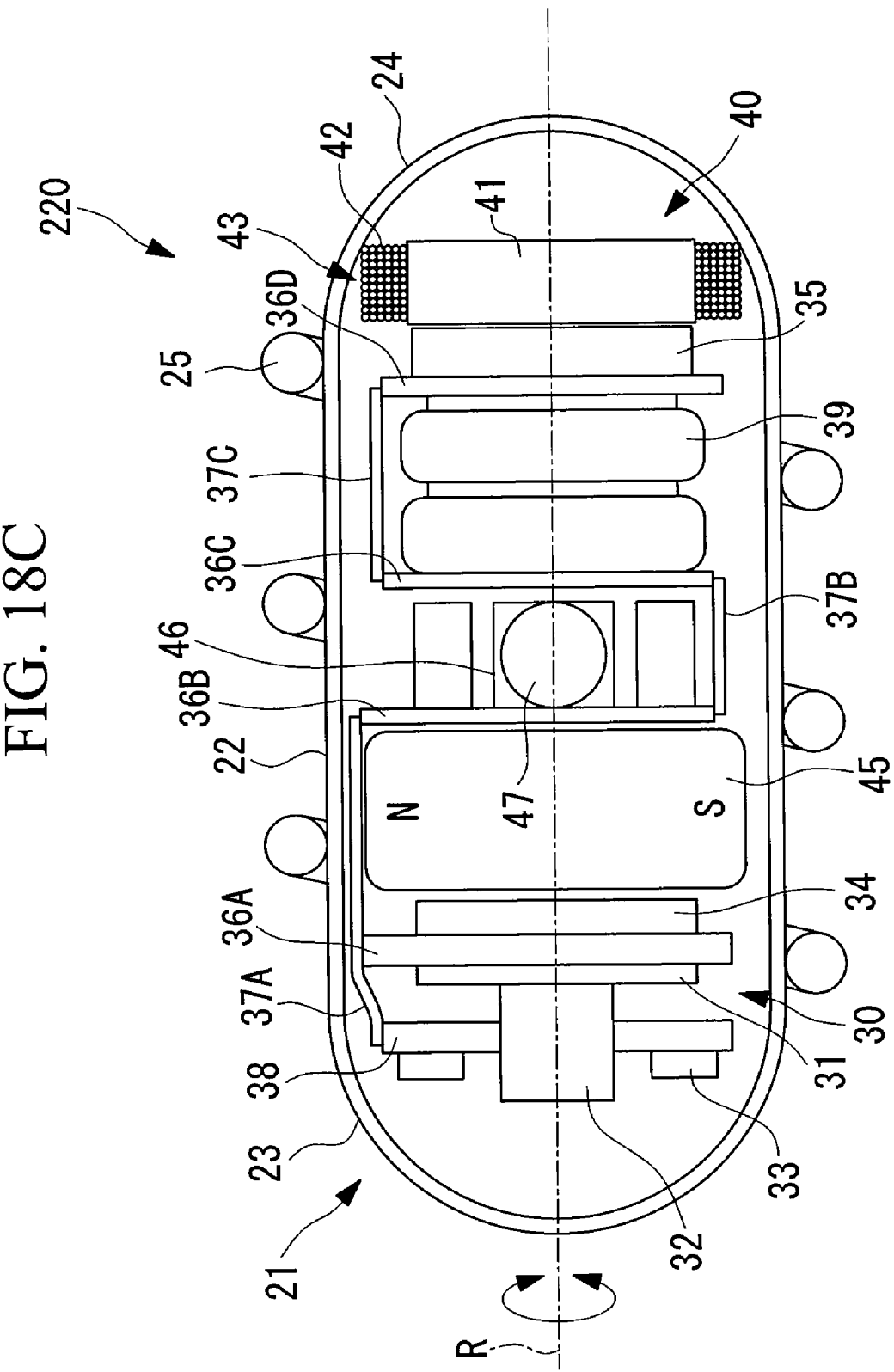
FIG. 18C illustrates the structure of a capsule endoscope shown in FIG. 15.

FIG. 18C illustrates the structure of the capsule endoscope shown in FIG. 15.

As shown in FIG. 18C, the capsule endoscope 220 is mainly formed of an outer casing 21 that accommodates various devices in the interior thereof; an image-acquisition section 30 that images an internal surface of a passage in the body cavity of the subject; a battery 39 for driving the image-acquisition section 30; an induced-magnetic-field generating section 40 that generates induced magnetic fields by means of the drive coils 51 described above; and a driving magnet (induction magnet) 45 for driving the capsule endoscope 220.

Since the image-acquisition section 30 and the induced-magnetic-field generating section 40 are the same as those in the first embodiment, descriptions of their structures, operations, and effects are omitted here.

A helical part 25 in which a wire having a circular cross-section is wound in the form of a helix about the rotation axis R is provided on the outer circumferential surface of the main body of the outer casing 21.

The driving magnet 45 is disposed on the rear end portion 24 side of a signal processing section 34, and switch sections 46 are disposed on a substrate 36B on the rear end portion 24 side of the driving magnet 45.

As shown in FIG. 16, the magnetic guidance device 270 is disposed below the subject 1 so that the magnetic guidance device 270 can move below the subject 1 in the back/forth and left/right directions independently of the position detection device 250.

The magnetic guidance device 270 is mainly formed of a plurality of electromagnets 701, 702, 703, 704, and 705. The electromagnets 701 and 702 face each other, with the electromagnet 705 interposed therebetween, and generate a magnetic field above the electromagnet 705 in the X-axis direction. The electromagnets 703 and 704 face each other, with the electromagnet 705 interposed therebetween, and generate a magnetic field above the electromagnet 705 in the Y-axis direction. The electromagnet 705 is surrounded by the electromagnets 701, 702, 703, and 704 and generates a magnetic field in the Z-axis direction. The magnetic guidance device 270 can form a uniform magnetic field in a cylindrical area above the electromagnet 705.

In the magnetic guidance device 270, the supplied current is controlled by the position detection device 250 that controls the intensity and the direction of the magnetic field formed by the electromagnets 701, 702, 703, 704, and 705.

The magnetic guidance device 270 is controlled by the position detection device 250 to move below the subject 1 in the back/forth and left/right directions.

FIG. 18A is a schematic view illustrating the structure of the position detection system shown in FIG. 15. FIG. 18B is a schematic view illustrating the entire structure of the position detection system shown in FIG. 15.

This embodiment is applied to the position detection system 210 including the electromagnets 701, 702, 703, 704, and 705, as described above. However, the configuration of the electromagnets is not limited thereto. For example, as shown in FIG. 18A, a position detection system 280 may use a triple-axis Helmholtz coil unit (magnetic-field generating section, electromagnet) 281 including three Helmholtz coils that generate parallel magnetic fields in pairs of coils, which are disposed facing each other. Instead, as shown in FIG. 18B, the position detection system 280 may use three pairs of substantially rectangular coils 281X and 281X, coils 281Y and 281Y, and coils 281Z and 281Z, which face each other. The intervals between the coils may be changed appropriately with respect to the diameter of the coils so long as a desired magnetic field is acquired in a certain space.

Furthermore, apart from coils facing each other, any other configuration may be employed so long as a desired magnetic field is obtained.

Next, the operation of the above-described position detection system 210 will be described.

Since the overall operation of the position detection system 210 is the same as that in the first embodiment, a description thereof is omitted here.

As described above, since the magnetic guidance device 270 forms a uniform magnetic field only in the cylindrical area above the electromagnet 705, the position detection device 250 moves the magnetic guidance device 270 in the back/forth and left/right directions so that the capsule endoscope 220 is positioned in the cylindrical area.

In the magnetic guidance device 270, the electric current supplied to the electromagnets (guidance-magnetic-field generating section) 701, 702, 703, 704, and 705 is controlled by the position detection device 250 so that a rotating magnetic field acts on the capsule endoscope 220. The capsule endoscope 220 is caused to rotate around the rotation axis R by the rotating magnetic field and move in the direction of the rotation axis R by the action of the helical part 25.

The magnetic guidance device 270 controls the rotation axis direction of the rotating magnetic field formed so as to control the direction of the rotation axis R of the capsule endoscope 220 and the traveling direction of the capsule endoscope 220.

With the above-described position detection system 210, the position and so on of the capsule endoscope 220 can be determined by the position detection system 210, and the capsule endoscope 220 can be guided to a predetermined position by the magnetic guidance device 270.

The magnetic field formed by the magnetic guidance device 270 also acts on the sense coils 52, and the AC voltage output from the sense coils 52 contains an AC voltage associated with the magnetic field. By separating the imaginary part of the AC voltage from the output at an amplitude-component detecting section 250A of the position detection device 250, it is possible to detect only the AC voltage associated with a LC resonance circuit 43. Consequently, even when the magnetic guidance device 270 is added, the position detection system 210 can calculate the position and so on of the capsule endoscope 220 without performing calibration measurement.

When the magnetic guidance device 270 is moved in the back/forth and left/right directions with respect to the sense coils 52, the AC voltage associated with the magnetic guidance device 270 output from the sense coils 52 according to the movement of the magnetic guidance device 270 also changes. In such a case, the position detection device 250 can detect only the AC voltage associated with the LC resonance circuit 43, without being affected by the change in the AC voltage. Consequently, even when the magnetic guidance device 270 is added, the position detection system 210 can calculate the position and so on of the capsule endoscope 220 without performing calibration measurement.

Since a calibration value measured in advance does not have to be stored, the system configuration can be simplified.

Fourth Embodiment

Next, a fourth embodiment of the present invention will be described with reference to FIGS. 19 and 20.

The basic structure of a position detection system according to this embodiment is the same as that according to the first embodiment, except that a plurality of capsule endoscopes is used. Therefore, in this embodiment, only the feature related to use of a plurality of capsule endoscopes will be described with reference to FIGS. 19 and 20, and descriptions of other components will be omitted here.

Figure 19:
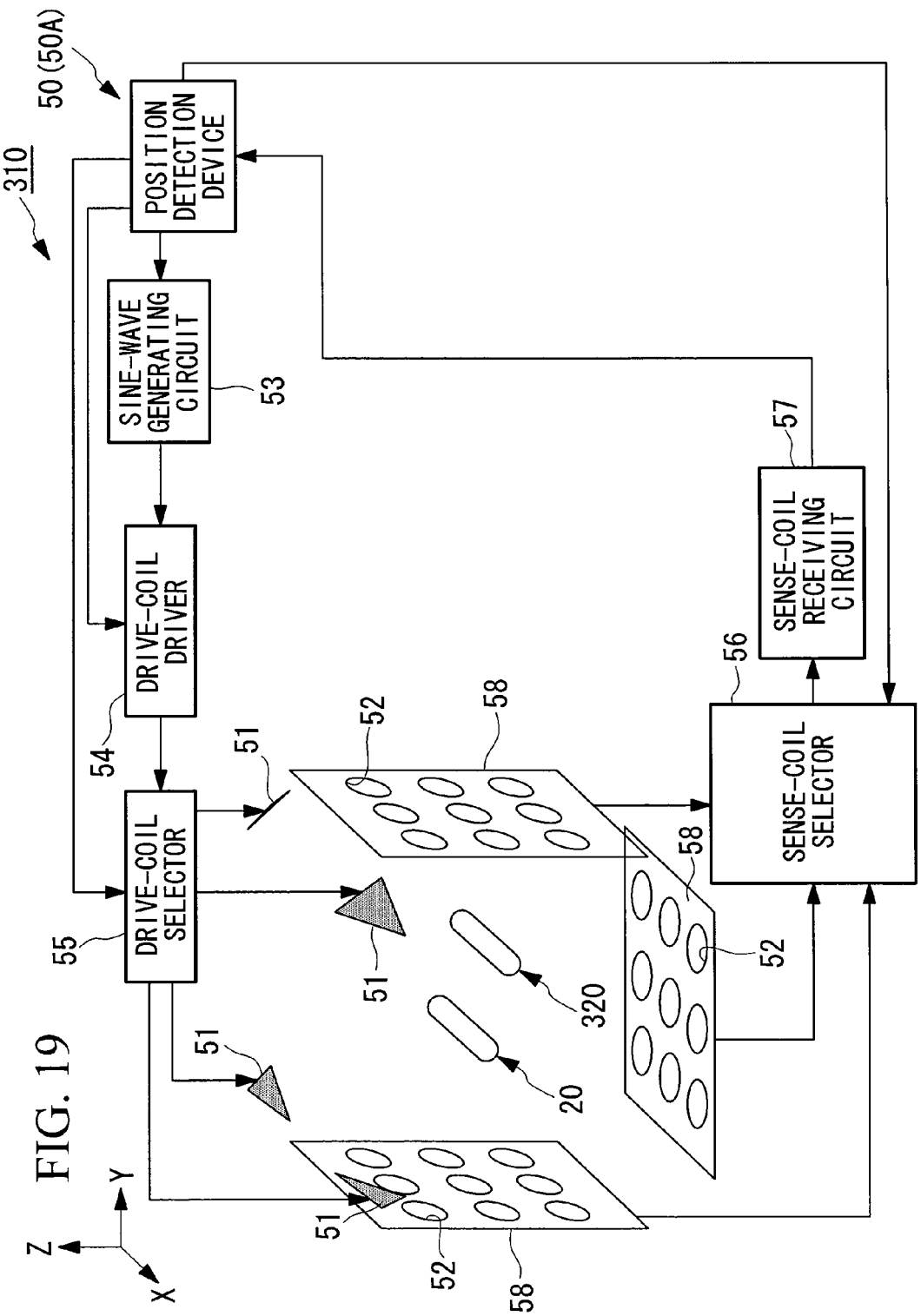
FIG. 19 is a block diagram illustrating, in outline, a position detection system according to a fourth embodiment of the present invention.

FIG. 19 is a block diagram illustrating, in outline, a position detection system according to this embodiment. FIG. 20 is a schematic view illustrating the structure of the position detection system shown in FIG. 19.

Components that are the same as those according to the first embodiment will be represented by the same reference numerals, and descriptions thereof will be omitted here.

Figure 20:
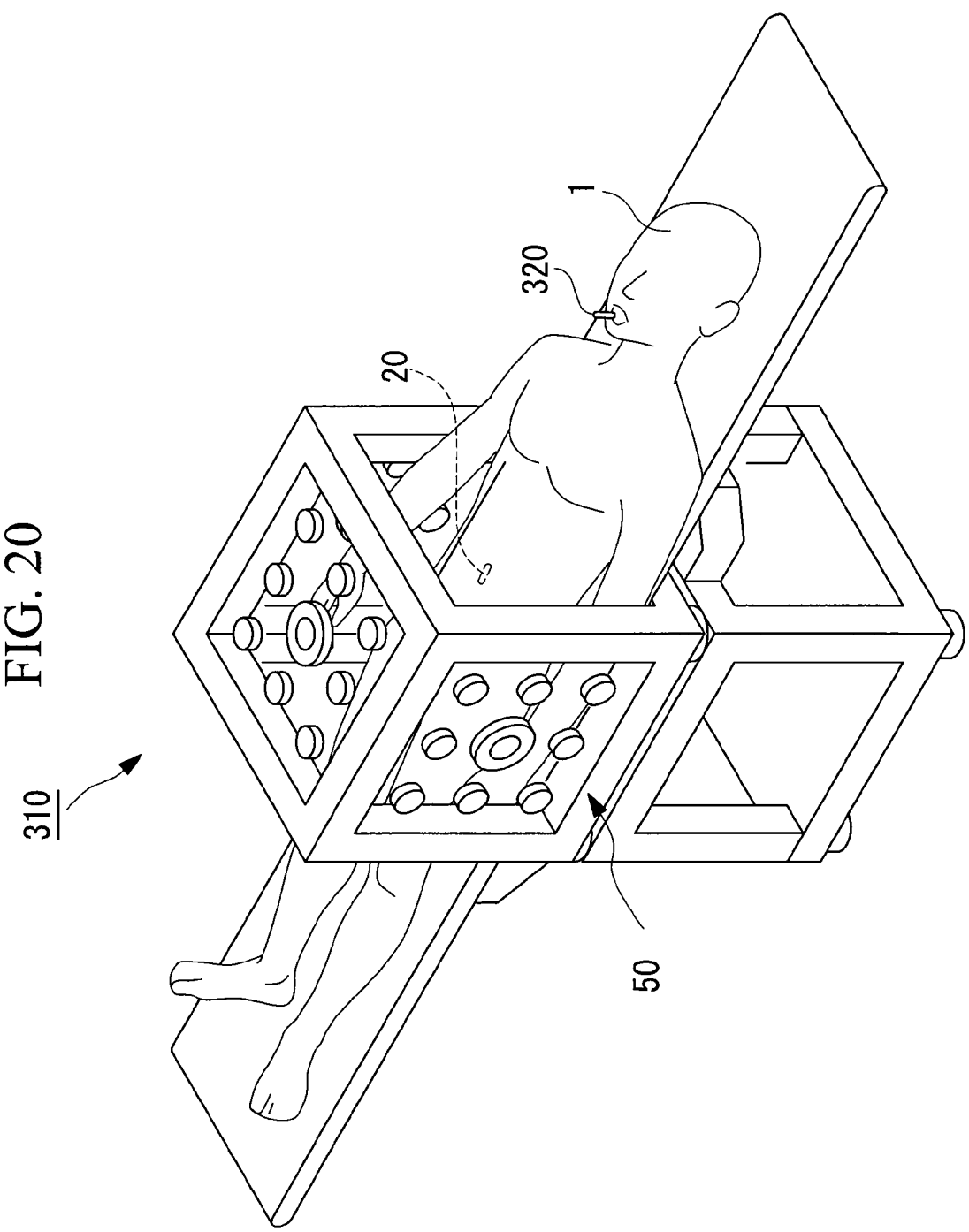
FIG. 20 is a schematic view illustrating the structure of the position detection system shown in FIG. 19.

As shown in FIGS. 19 and 20, a position detection system 310 is mainly formed of a capsule endoscope 20 that optically images an internal surface of a passage in the body cavity and wirelessly transmits an image signal, a capsule endoscope 320 that disperses a drug in a passage in the body cavity and collects a sample, and a position detection device 50 that detects the position of the capsule endoscope 20 and the capsule endoscope 320.

Similar to the capsule endoscope 20, the capsule endoscope 320 is mainly formed of a battery 39 for driving an internal device, an induced-magnetic-field generating section 40 that generates induced magnetic fields, and a medical device section (not shown) that disperses a drug (refer to FIG. 5).

The resonant frequency of the induced-magnetic-field generating section 40 in the capsule endoscope 20 is different from the resonant frequency of the induced-magnetic-field generating section 40 in the capsule endoscope 320.

Next, the operation of the position detection system 310, having the above-described structure, will be described.

Since the overall operation of the position detection system 310 is the same as that in the first embodiment, a description thereof is omitted here.

Examination of the inner surface of a passage in the body cavity is performed by the capsule endoscope 20 imaging the passage in the body cavity of the subject 1. An affected area may be found through the examination, and it may be necessary to administer a drug to the affected area and collect a sample. In such a case, the capsule endoscope 320 having functions of drug dispersal and sample collection is additionally introduced into the subject 1. In such a case, both the capsule endoscope 20 and the capsule endoscope 320 are present in the passage in the body cavity of the subject 1.

The position detection device 50 calculates the positions and so on of the capsule endoscope 20 and the capsule endoscope 320 using the resonant frequency of the LC resonance circuit 43 in the capsule endoscope 20 and the resonant frequency of the LC resonance circuit 43 in the capsule endoscope 320.

With the above-described position detection system 310, the amplitude-component detection section 50A in the position detection device 50 (see FIG. 6) can separate, from the AC voltage output from the sense coils 52, an imaginary part of the AC voltage associated with the LC resonance circuit 43 in the capsule endoscope 20 and the imaginary part of the AC voltage associated with the LC resonance circuit 43 in the capsule endoscope 320.

Therefore, even when the capsule endoscope 320 is additionally introduced, similar to the case with the capsule endoscope 20, the position and so on of the capsule endoscope 320 can be calculated without performing calibration measurement.

Fifth Embodiment

Next, a fifth embodiment of the present invention will be described with reference to FIGS. 21 to 25.

The basic structure of a position detection system according to this embodiment is the same as that according to the first embodiment, except that the process carried out at the position detection device differs. Therefore, in this embodiment, only the process carried out at the position detection device will be described with reference to FIGS. 21 to 25, and a description of the capsule endoscope and so on will be omitted here.

Figure 21:
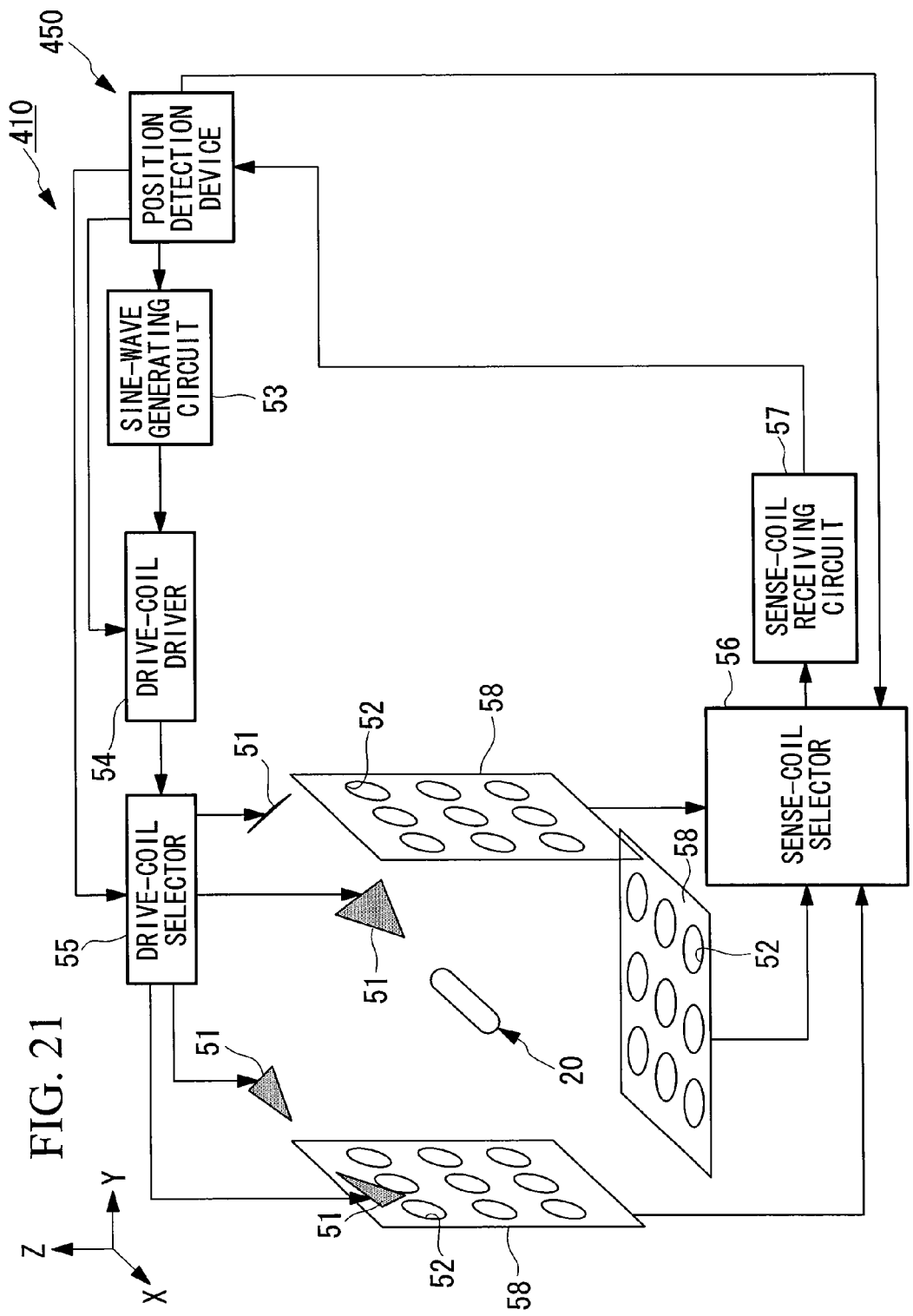
FIG. 21 is a block diagram illustrating, in outline, a position detection system according to a fifth embodiment of the present invention.

FIG. 21 illustrates, in outline, a position detection system according to this embodiment.

As shown in FIG. 21, a position detection system 410 is mainly formed of a capsule endoscope 20 and a position detection device (position-calculating-frequency determining section, reference-value-calculating-frequency determining section, measurement-reference-value calculating section, position analyzing section) 450 that detects the position of the capsule endoscope 20.

As shown in FIG. 21, the position detection device 450 is electrically connected to drive coils (drive coils) 51 that generate an induced magnetic field at magnetic induction coils, described below, in the capsule endoscope 20 and sense coils 52 that detect the induced magnetic field generated at the magnetic induction coils. The position detection device 450 calculates the position of the capsule endoscope 20 on the basis of the induced magnetic field detected by the sense coils 52 and controls the alternating magnetic field formed by the drive coils 51.

Figure 22:
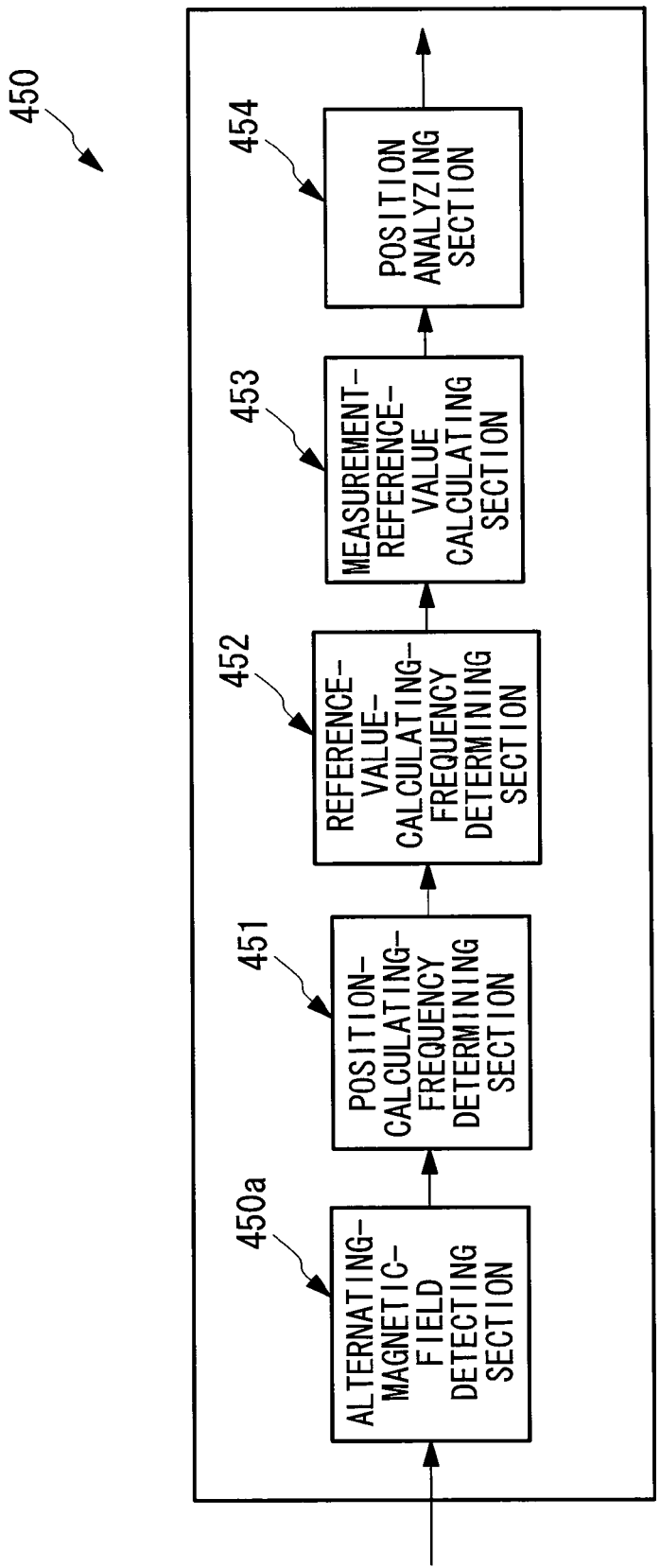
FIG. 22 is a block diagram illustrating the structure inside a position detection device shown in FIG. 21.

FIG. 22 is a block diagram illustrating the structure inside the position detection device shown in FIG. 21.

The position detection device 450 is provided with an alternating-magnetic-field detecting section 450a that detects an amplitude value of an alternating magnetic field of an AC voltage output from the sense coils 52 (outputs of magnetic-field sensors); a position-calculating-frequency determining section 451 that determines position-calculating frequencies (first frequency) $f_H$ and $f_L$ used for calculating the position and so on of the capsule endoscope 20; a reference-value-calculating-frequency determining section (reference-value-calculating-frequency determining section) 452 that determines a reference-value-calculating frequency (second frequency) $f_1$ used for calculating reference values; a measurement-reference-value calculating section (measurement-reference-value calculating section) 453 that calculates measurement reference values from the outputs of the sense coils 52 at the position-calculating frequencies $f_H$ and $f_L$ and the reference-value-calculating frequency $f_1$; and a position analyzing section (position analyzing section) 454 that calculates the position and so on of the capsule endoscope 20.

Next, the operation of the position detection system 410, having the above-described structure, will be described.

Since the overall operation of the position detection system 410 is the same as that in the first embodiment, a description thereof is omitted here.

Next, the operation of the position detection system 410 characterizing this embodiment will be described.

Then, the operation of the position detection device 450 characteristic to this embodiment will be described.

Since the procedures of generating an alternating magnetic field at the drive coils 51, detecting the induced magnetic field formed at the LC resonance circuit 43 (see FIG. 5) of the capsule endoscope 20 by the sense coils 52, and inputting the AC voltages output from the sense coils 52 to the position detection device 450 are the same as those in the first embodiment, descriptions thereof are omitted here.

Figure 23:
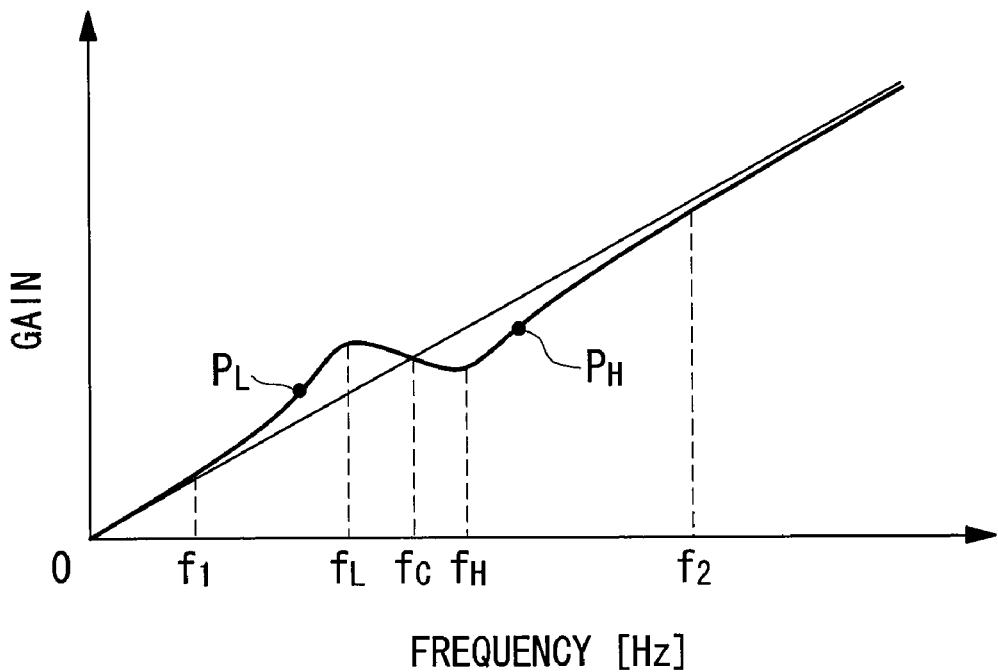
FIG. 23 is a graph illustrating a frequency characteristic of an AC voltage output from sense coils shown in FIG. 21.

FIG. 23 is a graph illustrating the frequency characteristic of an AC voltage output from the sense coils shown in FIG. 21.

As shown in FIG. 22, an AC voltage input to the position detection device 450 is input to the alternating-magnetic-field detecting section 450a. The alternating-magnetic-field detecting section 450a detects the amplitude values of the alternating magnetic field by Fourier transformation. The detected amplitude values of the alternating magnetic field are input to the position-calculating-frequency determining section 451. As shown in FIG. 23, the position-calculating-frequency determining section 451 detects the frequencies corresponding to the maximum and minimum values of the AC voltage, near a resonant frequency $f_C$ of the LC resonance circuit 43 of the capsule endoscope 20. The frequencies corresponding to the maximum and minimum values are defined as the position-calculating frequencies $f_H$ and $f_L$, respectively.

One of the position-calculating frequencies $f_H$ and $f_L$ is on the lower frequency side of the resonant frequency $f_C$ and the other is on the higher frequency side.

The reference-value-calculating-frequency determining section 452 defines a frequency on the frequency characteristic curve of the AC voltage of the induced magnetic field obtained by the position analyzing section 454, described below, as a reference-value calculating frequency $f_1$ that is on the lower frequency side far away from an inflection point $P_L$, which is on the lower frequency side of the resonant frequency $f_C$, and that is higher than the frequency of a commercial power supply (60 Hz or 50 Hz).

Figure 24:
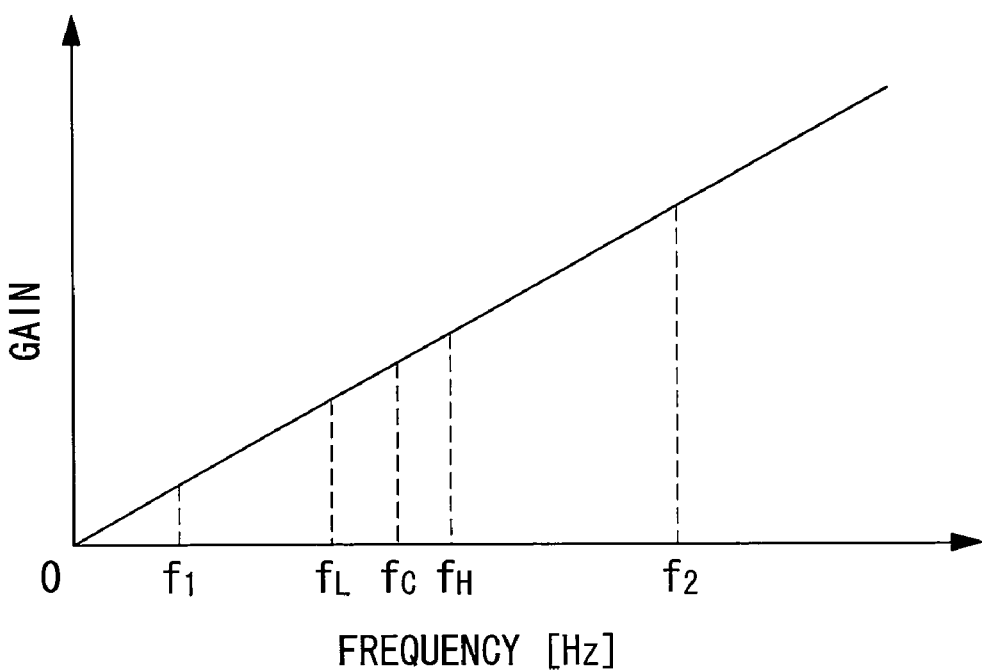
FIG. 24 is a graph illustrating the AC-voltage frequency characteristic of the sense coils shown in FIG. 21 when only an alternating magnetic field acts upon the sense coils.

FIG. 24 is a graph illustrating the AC-voltage frequency characteristic of the sense coils 52 shown in FIG. 21 when only an alternating magnetic field acts upon the sense coils 52.

The measurement-reference-value calculating section 453 calculates measurement reference values from the values of the AC voltage output from the sense coils 52 at the position-calculating frequencies $f_H$ and $f_L$ and the reference-value calculating frequency $f_1$. More specifically, the measurement-reference-value calculating section 453 determines the values of the AC voltages output from the sense coils 52 at the position-calculating frequencies $f_H$ and $f_L$ and determines the average value thereof. Then, the measurement-reference-value calculating section 453 determines a reference value based on a point determined from an intermediate point between the position-calculating frequencies $f_H$ and $f_L$ and the average value, and a point determined from the reference-value calculating frequency $f_1$ and the value of the corresponding AC voltage. To determine reference values, an approximation method based on the least-squares method is used. Reference values determined in this way can be represented as a graph representing a predetermined frequency characteristic, as shown in FIG. 24. The reference values are values that can be assumed as corresponding to the AC voltage output from the drive coil 51 due to an alternating magnetic field formed by the drive coils 51.

The reference values may be approximated on the basis of two points, as described above, or may be approximated on the basis of two or more measurement points.

Figure 25:
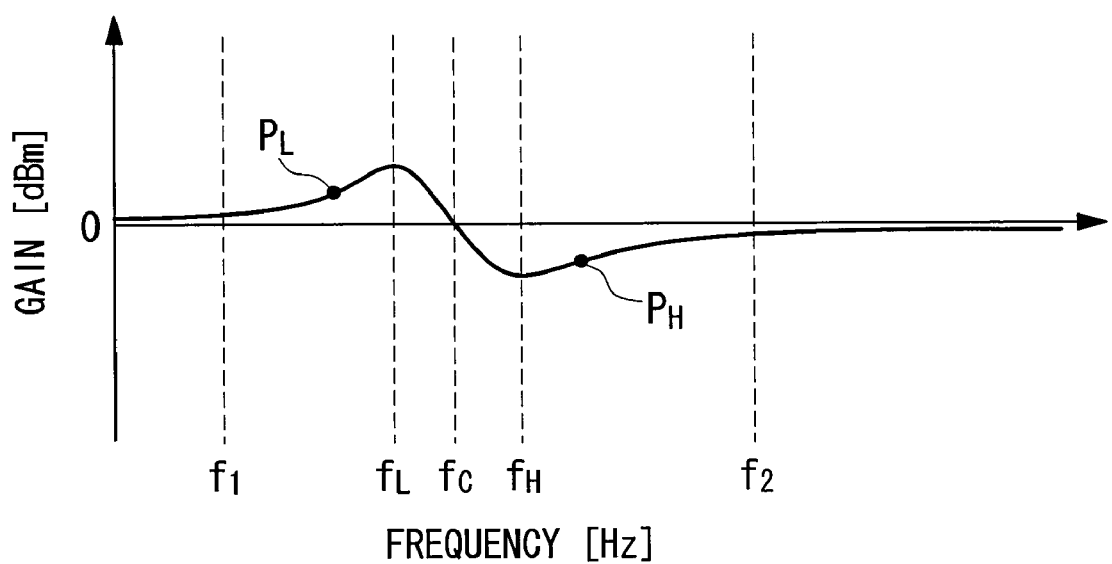
FIG. 25 is a graph illustrating the AC-voltage frequency characteristic of the sense coils shown in FIG. 21 when only induced magnetic field acts upon the sense coils.

FIG. 25 is a graph illustrating the AC-voltage frequency characteristic of the sense coils 52 shown in FIG. 21 when only an induced magnetic field acts upon the sense coils 52.

The position analyzing section 454 performs calculation for obtaining the differences of the above-described measurement reference values from the frequency characteristic curve of an AC voltage output from the sense coils 52 so as to obtain a frequency characteristic curve of an AC voltage due to an induced magnetic field, as shown in FIG. 25. The position analyzing section calculates 454 the difference in the AC voltage at the position-calculating frequencies $f_H$ and $f_L$, i.e., the amplitude, for each sense coil 52. After amplitude values for the sense coils 52 are obtained, the position and so on of the capsule endoscope 20 is calculated on the basis of these values.

With the above-described position detection system 410, the measurement-reference-value calculating section 453 can determine measurement reference values at the position-calculating frequencies on the basis of the output values of the sense coils 52 at the position-calculating frequencies $f_H$ and $f_L$ and the reference-value calculating frequency $f_1$, and the position analyzing section 454 can calculate the position and so on of the capsule endoscope 20 on the basis of the differences between the output values of the sense coils 52 and the measurement reference values when an alternating magnetic field and an induced magnetic field act on the magnetic-field sensors. In other words, by calculating the differences between the output values of the sense coils 52 and the measurement reference values when the alternating magnetic field and the induced magnetic field act on the sense coils 52, output values associated with the induced magnetic field can be extracted from the output values of the sense coils 52, and the position and so on of the capsule endoscope 20 can be calculated.

Therefore, the position detection system 410 can calculate the position and so on of the capsule endoscope 20 without performing calibration measurement.

A power source does not have to be added to the LC resonance circuit 43 of the capsule endoscope 20 because an induced magnetic field is generated by the alternating magnetic field. Therefore, the number of components to be installed inside the capsule endoscope 20 can be reduced. Since the power source installed inside is not used because an induced magnetic field used for position detection of the capsule endoscope 20 generated, the life of the capsule endoscope 20 is not affected by the life of the power source.

Since the position-calculating frequencies $f_H$ and $f_L$ are used to determine the measurement reference values, measurements associated with calculating the position and so on of the capsule endoscope 20 and measurements for determining the measurement reference values can be carried out simultaneously. In this way, the amount of work required for calculating the position and so on of the capsule endoscope 20 can be reduced.

By using two different position-calculating frequencies $f_H$ and $f_L$, errors in the measurement values can be canceled out compared with when output values at one frequency are used. In this way, the accuracy of the calculated position and so on of the capsule endoscope 20 can be improved.

With the alternating-magnetic-field detecting section 450a, instead of using Fourier transformation, at least one of a phase detector and a lock-in amplifier may be provided. By provided at least one of a phase detector and a lock-in amplifier in the alternating-magnetic-field detecting section 450a, the alternating-magnetic-field detecting section 450a can easily detect at least one of the imaginary part and the real part of the alternating magnetic field from the outputs from the magnetic-field sensors, obtained from a plurality of sense coils 52.

As described above, the reference-value calculating frequency $f_1$ may be a predetermined frequency higher than the frequency of a commercial power supply or may be zero.

When the frequency is zero, the outputs of the sense coils 52 are constantly zero. Therefore, the measurement associated with the reference-value calculating frequency $f_1$ can be omitted. In this way, the amount of work required for calculating the position and so on of the capsule endoscope 20 can be reduced.

As described above, the reference-value calculating frequency $f_1$ may be a predetermined frequency that is on the lower frequency side of the inflection point $P_L$ with respect to the resonant frequency $f_C$ and that is higher than the frequency of a commercial power supply. Instead, the reference-value calculating frequency $f_1$ may be a predetermined frequency $f_2$ that is higher than an inflection point $P_H$ on the higher frequency side with respect to the resonant frequency $f_C$ and that is lower than the resonant frequency of the sense coils 52.

Modification of Fifth Embodiment

Next, a modification of the fifth embodiment of the present invention will be described with reference to FIGS. 26 to 28.

The basic structure of a position detection system according to this embodiment is the same as that according to the fifth embodiment, except that the structures of the position detection device and the sense-coil receiving circuit differ. Therefore, in this embodiment, only the structures of the position detection device and the sense-coil receiving circuit will be described with reference to FIGS. 26 to 28, and a description of the capsule endoscope and so on will be omitted here.

Figure 26:
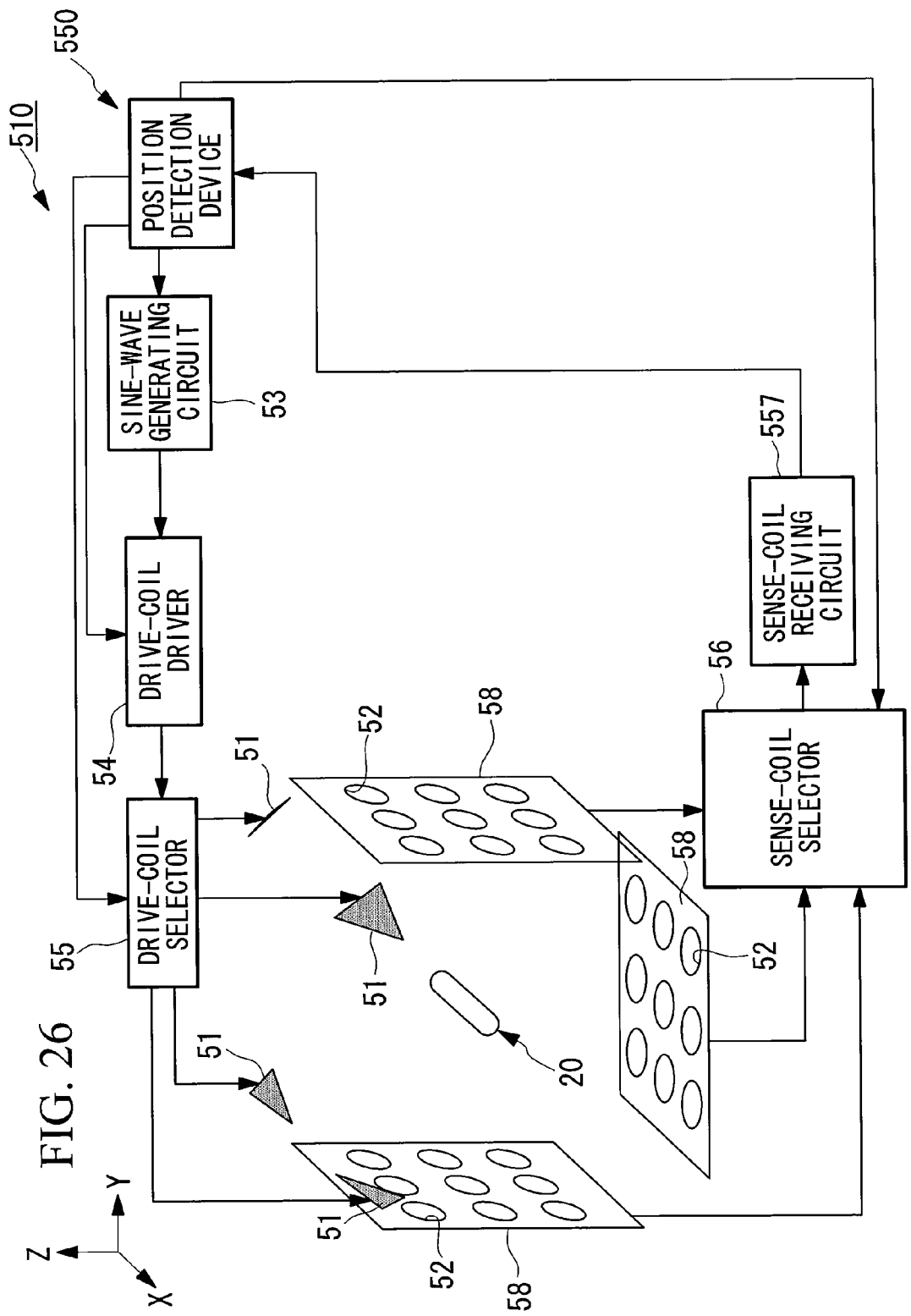
FIG. 26 illustrates the overall structure of a position detection system according to a modification of the fifth embodiment.

FIG. 26 illustrates the overall structure of a position detection system according to this modification of the fifth embodiment.

Components that are the same as those according to the fifth embodiment will be represented by the same reference numerals, and descriptions thereof will be omitted here.

As shown in FIG. 26, a position detection system 510 is mainly formed of a capsule endoscope 20 and a position detection device (position-calculating-frequency determining section, reference-value-calculating-frequency determining section, measurement-reference-value calculating section, position analyzing section) 550 that detects the position of the capsule endoscope 20.

As shown in FIG. 26, the position detection device 550 is electrically connected to drive coils (drive coils) 51 that generate an induced magnetic field at magnetic induction coils, described below, in the capsule endoscope 20 and sense coils 52 that detect the induced magnetic field generated at the magnetic induction coils. The position detection device 550 calculates the position of the capsule endoscope 20 on the basis of the induced magnetic field detected by the sense coils 52 and controls the alternating magnetic field formed by the drive coils 51.

Figure 27:
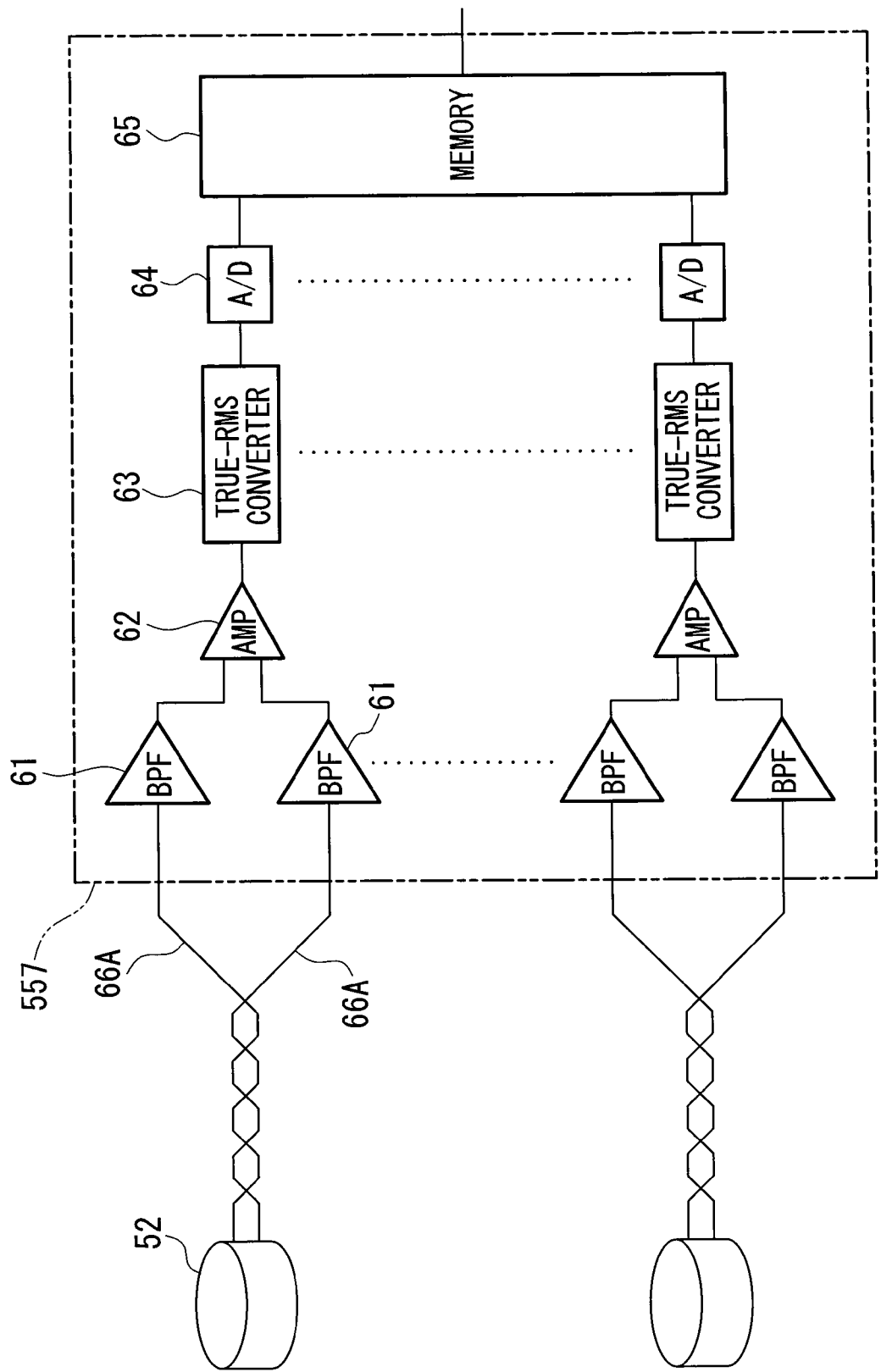
FIG. 27 illustrates the circuitry of a sense-coil receiving circuit shown in FIG. 26.

FIG. 27 illustrates the circuitry of a sense-coil receiving circuit 557 shown in FIG. 26.

As shown in FIG. 27, the sense-coil receiving circuit 557 is formed of band-pass filters (BPF) 61 that remove high-frequency components and low-frequency components included in the AC voltages including the input position information of the capsule endoscope 20; amplifiers (AMP) 62 that amplify the AC voltages from which the high-frequency components and low-frequency components have been removed; effective-value detection circuits (True RMS converters) 63 that detect the amplitudes of the AC voltages and extract and outputs the amplitude values; A/D converters 64 that convert the amplitude values to digital signals; and a memory 65 for temporarily storing the digitized amplitude values.

The band-pass filters 61 are disposed in the pair of wires 66A, respectively, that extend from each sense coil 52, and the AC voltages output from the band-pass filters 61 are input to the single amplifier 62. The memory 65 temporarily stores the amplitude values obtained from the nine sense coils 52 and outputs the stored amplitude values to the position detection device 550.

As described above, the effective-value detection circuits 63 may be used to extract the amplitude values of the AC voltages, rectification circuits may be used to detect the amplitude values by smoothing magnetic information and detecting the voltages, or peak-detection circuits that detect the peaks of the AC voltages may be used to detect the amplitude values.

Regarding the waveform of the detected AC voltage, the phase with respect to a waveform applied to the drive coil 51 changes depending on the presence and the position of a magnetic induction coil 42, described below, in the capsule endoscope 20. This phase change may be detected with a lock-in amplifier or the like.

The induced magnetic field generates an induced electromotive force in the sense coils 52, and an AC voltage (magnetic information) including position information of the capsule endoscope 20 is generated at the sense coils 52. This AC voltage is input to the sense-coil receiving circuit 557 via the sense-coil selector 56, and the amplitude value (amplitude information) of the AC voltage is extracted.

As shown in FIG. 27, high-frequency components and low-frequency component of the AC voltage input to the sense-coil receiving circuit 557 are removed by the band-pass filters 61, and then the AC voltage is amplified by the amplifier 62. The amplitude value of the AC voltage is extracted from the AC voltage having unwanted components removed therefrom, by the effective-value detection circuits 63. The extracted amplitude value is converted to a digital signal at the A/D converters 64 and is stored in the memory 65.

The memory 65 stores amplitude values corresponding to, for example, one sweep cycle in which a sine-wave signal generated in the sine-wave generating circuit 53 is swept near the resonance frequency of the LC resonance circuit 43 and outputs the amplitude values of one cycle as a group to the position detection device 550.

Figure 28:
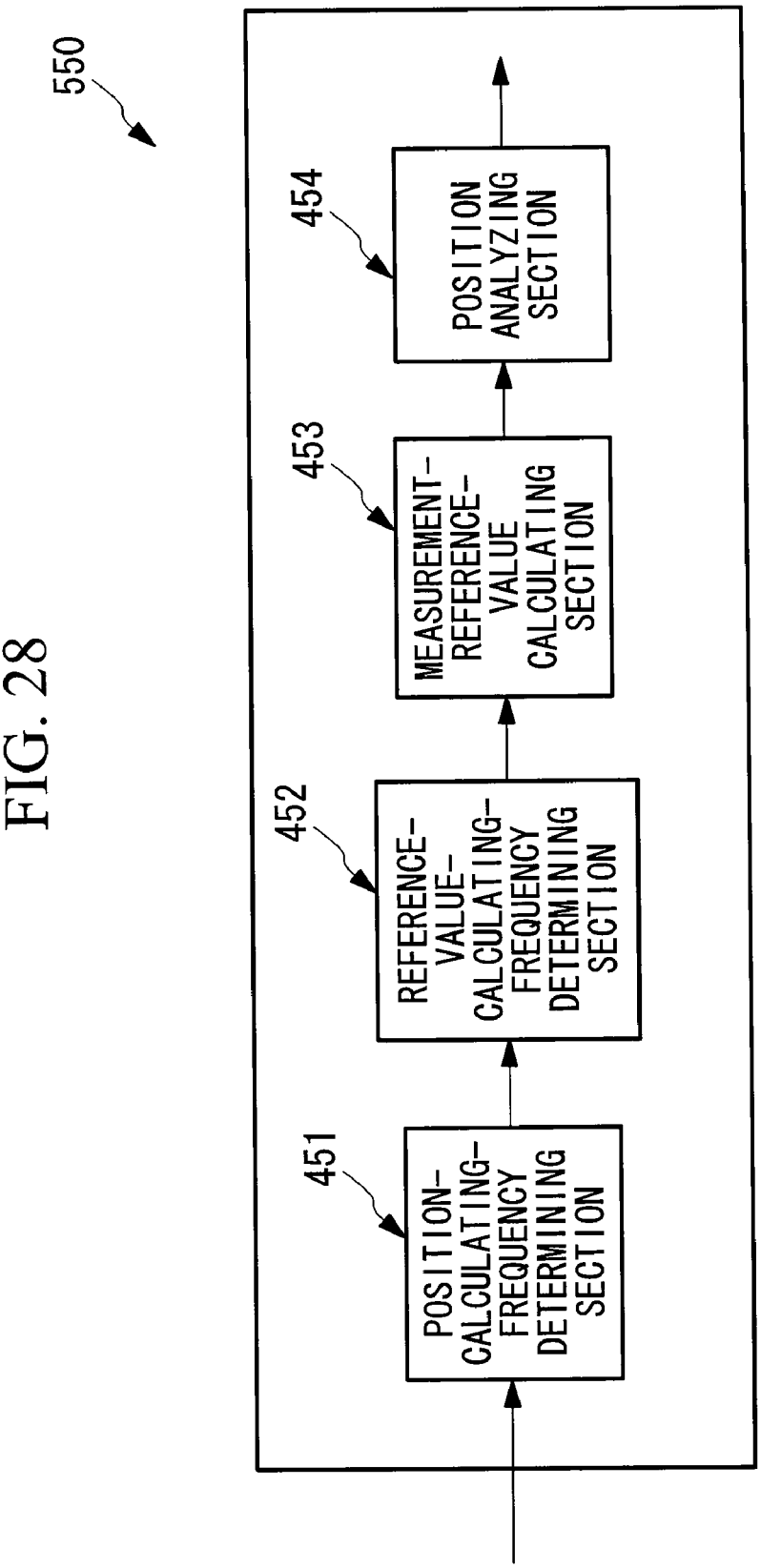
FIG. 28 is a block diagram illustrating, in outline, a position detection device shown in FIG. 26.

FIG. 28 is a block diagram illustrating, in outline, the position detection device 550 shown in FIG. 26.

The position detection device 550 is provided with a position-calculating-frequency determining section 451 that determines position-calculating frequencies (first frequency) $f_H$ and $f_L$, used for calculating the position and so on of the capsule endoscope 20; a reference-value-calculating-frequency determining section (reference-value-calculating-frequency determining section) 452 that determines a reference-value-calculating frequency (second frequency) $f_1$ used for calculating reference values; a measurement-reference-value calculating section (measurement-reference-value calculating section) 453 that calculates measurement reference values from the outputs of the sense coils 52 at the position-calculating frequencies $f_H$ and $f_L$ and the reference-value-calculating frequency $f_1$; and a position analyzing section (position analyzing section) 454 that calculates the position and so on of the capsule endoscope 20.

As shown in FIG. 28, an AC voltage input to the position detection device 550 is input to the position-calculating-frequency determining section 451. As shown in FIG. 23, the position-calculating-frequency determining section 451 detects the frequencies corresponding to the maximum and minimum values of the AC voltage, near a resonant frequency $f_C$ of the LC resonance circuit 43 of the capsule endoscope 20. The frequencies corresponding to the maximum and minimum values are defined as the position-calculating frequencies $f_H$ and $f_L$, respectively. The outline of the operations executed in sections from the reference-value-calculating-frequency determining section 452 to the position analyzing section 454 is the same as that in the fifth embodiment, and therefore, a description thereof is omitted here.

As described above, the reference value is not particularly limited and may be determined using the position-calculating frequencies $f_H$ and $f_L$ and the reference-value calculating frequency $f_1$, or may be determined using the above-mentioned predetermined frequency $f_2$ and the reference-value calculating frequency $f_1$.

According to this modification, since the sense-coil receiving circuit 557 includes the effective-value detection circuits 63, the alternating-magnetic-field detecting section 450a is not required. Thus, the position detection system can be produced at low cost.

All of the embodiments have been described in terms of a capsule endoscope and a capsule medical device. However, the embodiments are not particularly limited thereto, and any medical device that can be used in a body cavity, such as an endoscope, a catheter device, a clamp, or the like, may be employed. Furthermore, combinations of the embodiments are also included in the scope of the invention.

The invention claimed is:

1. A position detection system comprising:
a device having a magnetic inductance coil;
a drive coil configured to generate an alternating magnetic field;
a plurality of magnetic-field sensors disposed outside an operating range of the device and configured to detect an induced magnetic field generated by the magnetic inductance coil, which receives the alternating magnetic field;
a frequency determining section configured to determine a position-calculating frequency on the basis of a resonant frequency of the magnetic inductance coil;
amplitude-component detection section for detecting at least one of amplitude components substantially orthogonal to the alternating magnetic field and amplitude components having substantially the same phase as the alternating magnetic field from outputs of the plurality of magnetic-field sensors at the position-calculating frequency; and
position analyzing section for calculating at least one of a position and an orientation of the device on the basis of the amplitude components.

2. The position detection system according to claim 1, wherein the frequency determining section determines the position-calculating frequency by acquiring information about the resonant frequency in advance.

3. The position detection system according to claim 1, wherein the frequency determining section detects a change in the resonant frequency and determines the position-calculating frequency on the basis of the change.

4. The position detection system according to claim 1, wherein, when the amplitude-component detection section uses Fourier transformation to repeatedly calculate at least one of the position and the orientation of the device on the basis of the detected amplitude components, the amplitude-component detection section performs Fourier transformation while assuming that the difference between the timing of starting Fourier transformation and the phase of the alternating magnetic field generated by the drive coil is constant.

5. The position detection system according to claim 1, wherein the drive coil and the magnetic-field sensors are provided as separate bodies.

6. The position detection system according to claim 1, wherein the plurality of magnetic-field sensors is provided as a single body.

7. The position detection system according to claim 1, further comprising:
a drive-coil driver configured to change at least one of the direction and the intensity of the alternating magnetic field generated at the drive coil in accordance with the relative position of the drive coil and the magnetic inductance coil.

8. The position detection system according to claim 1, wherein the drive coil and the magnetic-field sensors are attached to a subject disposed in the operating range.

9. The position detection system according to claim 1, wherein, when a plurality of the devices is used simultaneously, the magnetic inductance coils installed in the devices are set to different resonant frequencies.

10. A guidance system comprising:
a position detection system comprising:
a device having a magnetic inductance coil; a drive coil configured to generate an alternating magnetic field; a plurality of magnetic-field sensors disposed outside an operating range of the device and configured to detect an induced magnetic field generated by the magnetic inductance coil, which receives the alternating magnetic field;
a frequency determining section configured to determine a position-calculating frequency on the basis of a resonant frequency of the magnetic inductance coil; an amplitude-component detection section for detecting at least one of amplitude components substantially orthogonal to the alternating magnetic field and amplitude components having substantially the same phase as the alternating magnetic field from outputs of the plurality of magnetic-field sensors at the position-calculating frequency; a position analyzing section for calculating at least one of a position and an orientation of the device on the basis of the amplitude components;
a guidance magnet installed in the device;
guidance-magnetic-field generating section for generating a guidance magnetic field that acts on the guidance magnet; and
guidance-magnetic-field-direction control section for controlling the direction of the guidance magnetic field.

11. The guidance system according to claim 10, wherein the guidance-magnetic-field generating section includes three pairs of electromagnets that are disposed facing each other in an orthogonally intersecting manner,
wherein a space where the subject lies is provided on the inner side of the electromagnets, and
wherein the drive coil and the magnetic-field sensors are disposed around the space where the subject lies.

12. The guidance system according to claim 10, wherein a helical part configured to convert a rotational force around the longitudinal axis of the device to a propulsive force along the longitudinal axis is provided on an outer surface of the device.

13. A position detection system comprising:
a device having a magnetic inductance coil;
a drive coil configured to generate an alternating magnetic field;
a plurality of magnetic-field sensors disposed outside an operating range of the device and configured to detect an induced magnetic field generated by the magnetic inductance coil, which receives the alternating magnetic field;
a frequency determining section configured to determine a position-calculating frequency on the basis of a resonant frequency of the magnetic inductance coil;
amplitude-component detection section for detecting at least one of amplitude components substantially orthogonal to the alternating magnetic field and amplitude components having substantially the same phase as the alternating magnetic field from outputs of the plurality of magnetic-field sensors at the position-calculating frequency; and
position analyzing section for calculating at least one of a position and an orientation of the device on the basis of the amplitude components, wherein the device comprises a capsule medical device.

14. A position detection system comprising:
a device having a magnetic inductance coil;
a drive coil configured to generate an alternating magnetic field;
a plurality of magnetic-field sensors configured to detect an induced magnetic field generated by the magnetic inductance coil, which receives the alternating magnetic field;
a frequency determining section configured to determine a position-calculating frequency on the basis of a resonant frequency of the magnetic inductance coil;
measurement-reference-value calculating section for determining a measurement reference value at the position-calculating frequency on the basis of outputs from the magnetic-field sensors output when the alternating magnetic field and the induced magnetic field are applied at a second frequency away from the position-calculating frequency; and
position analyzing section for calculating at least one of a position and an orientation of the device on the basis of a difference between the outputs from the magnetic-field sensors output when the alternating magnetic field and the induced magnetic field are applied at the position-calculating frequency and the measurement reference value.

15. The position detection system according to claim 14, wherein the position-calculating frequency is two different frequencies.

16. The position detection system according to claim 14, wherein the frequency determining section determines the position-calculating frequency by acquiring information about the resonant frequency of the magnetic inductance coil in advance.

17. The position detection system according to claim 14, wherein the frequency determining section detects a change in the resonant frequency of the magnetic inductance coil and determines the position-calculating frequency on the basis of the change.

18. The position detection system according to claim 14, wherein the drive coil and the magnetic-field sensors are provided as separate bodies.

19. The position detection system according to claim 14, wherein the plurality of magnetic-field sensors is provided as a single body.

20. The position detection system according to claim 14, wherein, when a plurality of the devices is used simultaneously, the magnetic inductance coils installed in the devices are set to different resonant frequencies.

21. The position detection system according to claim 14, wherein the device comprises a capsule medical device.

* * * * *